United States Patent
Baba et al.

(10) Patent No.: US 10,830,685 B2
(45) Date of Patent: Nov. 10, 2020

(54) DEVICE FOR ELECTRICAL MEASUREMENT AND ELECTRICAL MEASUREMENT APPARATUS

(71) Applicant: National University Corporation Nagoya University, Aichi (JP)

(72) Inventors: Yoshinobu Baba, Aichi (JP); Noritada Kaji, Aichi (JP); Takao Yasui, Aichi (JP); Tomoji Kawai, Osaka (JP); Takeshi Yanagida, Osaka (JP)

(73) Assignee: NATIONAL UNIVERSITY CORPORATION NAGOYA UNIVERSITY, Nagoya (JP)

( * ) Notice: Subject to any disclaimer, the term of this patent is extended or adjusted under 35 U.S.C. 154(b) by 375 days.

(21) Appl. No.: 15/565,031

(22) PCT Filed: Apr. 6, 2016

(86) PCT No.: PCT/JP2016/061225
§ 371 (c)(1),
(2) Date: Dec. 12, 2017

(87) PCT Pub. No.: WO2016/163387
PCT Pub. Date: Oct. 13, 2016

(65) Prior Publication Data
US 2018/0100792 A1   Apr. 12, 2018

(30) Foreign Application Priority Data

Apr. 7, 2015  (JP) .................................. 2015-078222
Dec. 14, 2015  (JP) .................................. 2015-243615

(51) Int. Cl.
*G01N 15/12* (2006.01)
*G01N 33/487* (2006.01)
(Continued)

(52) U.S. Cl.
CPC ..... *G01N 15/1218* (2013.01); *G01N 15/0656* (2013.01); *G01N 15/1031* (2013.01);
(Continued)

(58) Field of Classification Search
CPC ....... G01N 27/44791; G01N 27/44721; G01N 15/1218; G01N 15/1227; G01N 15/1031;
(Continued)

(56) References Cited

U.S. PATENT DOCUMENTS

2004/0118688 A1*  6/2004  Dumas ............. G01N 27/44704
                                                         204/548
2006/0194307 A1   8/2006  Yasuda et al.
(Continued)

FOREIGN PATENT DOCUMENTS

JP   01-235833 A   9/1989
JP   2006-180810 A   7/2006
(Continued)

OTHER PUBLICATIONS

Waseem et al., "Electrical fingerprinting, 3D profiling and detection of tumor cells with solid-state micropores" Lab Chip 12:2345-2352 (2012).
(Continued)

*Primary Examiner* — Gurpreet Kaur
(74) *Attorney, Agent, or Firm* — McDermott Will & Emery LLP

(57) ABSTRACT

Provided is a device for electrical measurement designed to be able to perform high sensitivity detection by reading not only changes in steady-state current, but also the occurrence of transient current, and an electrical measurement apparatus including the device for electrical measurement. The device for electrical measurement includes a substrate on which are formed at least a sample separation channel and a sample migration channel, as well as a sample measuring unit, with (Continued)

one end of the sample separation channel formed to connect to one end of the sample migration channel, and the sample measuring unit including a first measuring unit connected to the sample migration channel, and a second measuring unit connected to the sample migration channel from the reverse side to the first measuring unit.

11 Claims, 15 Drawing Sheets

(51) Int. Cl.
*G01N 27/447* (2006.01)
*G01N 15/10* (2006.01)
*G01N 15/06* (2006.01)
*G01N 15/00* (2006.01)

(52) U.S. Cl.
CPC ... *G01N 15/1227* (2013.01); *G01N 27/44721* (2013.01); *G01N 27/44791* (2013.01); *G01N 33/48721* (2013.01); *G01N 2015/0046* (2013.01); *G01N 2015/1006* (2013.01)

(58) Field of Classification Search
CPC .......... G01N 15/0656; G01N 33/48721; B01L 2400/0421; B01L 2400/0424; B01L 2200/0652; B01L 3/502761; B01L 3/502738; B01L 3/50273; B01L 2200/0684; B01L 2200/0668; B03C 5/00; B03C 5/022; B03C 5/024; B03C 5/026; Y10S 977/852; Y10S 977/733; Y10S 977/72; Y10S 977/721; C12Q 1/6813; C12Q 1/6876; C12Q 1/6825; C12Q 2563/116; C12Q 2565/631

See application file for complete search history.

(56) References Cited

U.S. PATENT DOCUMENTS

| | | | |
|---|---|---|---|
| 2011/0089328 A1* | 4/2011 | Li | B01L 3/50273 250/364 |
| 2012/0031176 A1* | 2/2012 | Naessens | B01L 3/5027 73/61.59 |
| 2013/0313113 A1 | 11/2013 | Koser | |
| 2014/0252505 A1 | 9/2014 | Kobayashi et al. | |
| 2015/0041316 A1* | 2/2015 | Miki | B01L 3/502753 204/406 |

FOREIGN PATENT DOCUMENTS

| | | |
|---|---|---|
| JP | 2014-500949 A | 1/2014 |
| JP | 2014-173935 A | 9/2014 |
| JP | 2015-36631 A | 2/2015 |

OTHER PUBLICATIONS

Naoya Y et al.,"Tracking single-particle dynamics via combined optical and electrical sensing" Scientific Reports, 3:1-7 (2013).

J.McGrath et al., "Deterministic lateral displacement for particle separation? a review" Lab on a Chip, 14:4139-4157 (2014).

Ikjoo Byun et al., "Transfer of thin Au films to polydimethylsiloxane (PDMS) with reliable bonding using (3-mercaptopropyl) trimethoxysilane (MPTMS) as a molecular adhesive"J. Micromech. Microeng. 23:1-10, 085016 (2013).

Written Opinion of the International Search Authority for PCT/JP2016/061225, dated Jun. 28, 2016.

Notice of Reasons for Refusal issued in corresponding Japanese Application No. 2017-511011, dated Dec. 2, 2019, with English machine translation.

* cited by examiner

DEVICE FOR ELECTRICAL MEASUREMENT AND ELECTRICAL MEASUREMENT APPARATUS

1. FIELD OF THE INVENTION

The present disclosure relates to a device for electrical measurement, and an electrical measurement apparatus, and particularly relates to a device for electrical measurement designed so that high sensitivity detection is possible by reading not only changes in steady-state current but also the occurrence of transient current when a sample such as of a cell, bacterium, virus, or DNA flows in a microchannel, and an electrical measurement apparatus including said device for electrical measurement.

2. DESCRIPTION OF THE RELATED ART

Accurate measurement of the size, number, etc., of samples of cells, bacteria, pollen, PM2.5, etc., contained in a solution is important information for leading a healthy lifestyle, and in recent years, there is even greater demand for improved measurement precision. Also, in the field of biochemistry, there is demand for development of an analytical device to analyze a DNA fragment without modification.

FIG. 1 shows prior art for a method for measuring the size, number, etc., of a sample, in which a sample is passed through fine pores (micropores) formed on a substrate of silicon, etc., and the size and hardness of cells are analyzed from the status of changes in steady-state current flowing inside the fine pores due to voltage applied to the fine pores (see Non-Patent Document 1). With the conventional measurement method shown in FIG. 1, it is known that the smaller the volume of the fine pores, the better the sensitivity. To reduce the volume of the fine pores, it is necessary to make the diameter smaller as well as make the substrate thinner, and because of that, the substrate is used standing vertically as shown in FIG. 1 during measurement.

Also, to measure the state of the sample passing through the fine pores in more detail, a method is also known of making it possible to observe the fine pore part using a fluorescence microscope by orienting the substrate that forms a microchannel horizontally, and, in addition to measuring the steady-state current, directly observing phenomena around the fine pores (see Non-Patent Document 2). FIG. 2 shows FIG. 1 of Non-Patent Document 2.

PRIOR ART DOCUMENTS

Non-Patent Documents

[Non-patent Document 1] Waseem A. et al., Lab on a Chip, Vol. 12, pp. 2345-2352 (2012)

[Non-patent Document 2] Naoya. Y et al., "Tracking single-particle dynamics via combined optical and electrical sensing", SCIENTIFIC REPORTS, Vol. 3, pp. 1-7(2013)

SUMMARY OF THE INVENTION

Problems to be Solved by the Invention

However, with the method shown in FIG. 1, the only information that is obtained is a signal of a change in steady-state current, and differentiation of the samples that passed through the fine pores is just inferring from the strength of the current value, etc. Thus, when a plurality of samples flow into the fine pores, or when the shape of the biomolecule, etc., which is the sample being measured is other than a sphere, or changes easily, etc., a problem is presented in regard to the difficulty of performing detailed analysis (Problem 1).

Also, with the method noted in Non-Patent Document 1, the drive circuit for driving the sample and the measuring circuit for measuring the current change when the sample passes through the fine pores are the same. Typically, it is possible to increase the measurement sensitivity by making the applied voltage greater, but when the drive circuit and the measurement circuit are the same, if the applied voltage is increased, a problem is presented in that there is too great a load on the ammeter of the measuring circuit, and high sensitivity detection is not possible (Problem 2).

Furthermore, the time for the sample to pass through the fine pores is affected by, inter alia, the surface charge or deformability of the sample, so particularly for biomolecule analysis, this is extremely important information. However, with the sensitivity of the conventional method, it is only possible to read gentle changes in the steady-state current within the fine pores, and there were large errors in reading of the time passing through short fine pores by samples accelerated by applied voltage. Additionally, when measuring a biomolecule with a long, thin shape such as nucleic acid, it is necessary to introduce the biomolecule in the fine pores in a stretched state, but to do that, a guide channel is necessary to put the biomolecule in a stretched state. However, to provide the guide channel, the volume of the fine pore part increases, and there is an unavoidable problem of a decrease in sensitivity (Problem 3).

On the one hand, as shown in FIG. 2, by placing the substrate horizontally and observing with a fluorescence microscope, it is possible to resolve the abovementioned Problem 1. However, the method noted in Non-Patent Document 2 is designed so that a sample dispersed in a liquid by pump pressure is passed through fine pores formed in a substrate. When flowing the sample dispersed in the liquid by pump pressure, reducing the fine pore size in order to increase measurement sensitivity results in greater difficulty for the liquid to flow through the fine pores. As shall be apparent, it is possible to flow the liquid by increasing the pump pressure, but when the pressure is too great, there is a risk of damaging the fine pore part. Also, with the method of flowing the sample by pump pressure noted in Non-Patent Document 2, there is a problem of not being able to flow nucleic acid or protein. Furthermore, with the method noted in Non-Patent Document 2, as with the method noted in Non-Patent Document 1, it is necessary to reduce the fine pore volume to increase sensitivity, and a problem is presented of not being able to resolve the abovementioned Problem 3.

The present disclosure was contrived to address the abovementioned prior art problems, and as a result of thoroughgoing studies, the following points were newly discovered:

(1) by forming a sample migration channel in which a sample can flow, and forming a first measuring unit connected to the sample migration channel and a second measuring unit connected to the sample migration channel from the reverse side to the first measuring unit, the sample drive circuit and measuring circuit can be designed as separate circuits;

(2) by having the sample drive circuit and the measuring circuit be separate circuits, the detection sensitivity can be increased by setting the voltage of the drive circuit high, and transient current which was buried in noise in the past can be measured;

(3) when a variable resistor is incorporated in the measuring circuit, higher sensitivity detection is possible, and transient current can be measured with better precision;

(4) by reading the transient current, it is possible to accurately measure the input/output timing of the sample to the sample migration channel, and as a result, the surface charge and deformability of the sample can be measured by calculating the sample passage rate;

(5) when the sample separation channel is formed before the sample migration channel, components not subject to analysis can be removed from the input sample; and (6) when sample collecting apparatus are formed to collect samples, harmful and hazardous substances floating in air or water can be collected and input to a sample input channel, so automatic analysis of harmful and hazardous substances in one's surroundings is possible.

Specifically, the purpose of the disclosure is to provide a device for electrical measurement that is able to do high sensitivity detection by reading not only changes in steady-state current but also the occurrence of transient current, and also is designed to be able to separate and remove components not subject to analysis, and automatically collect and analyze samples, as well as an electrical measurement apparatus including said device for electrical measurement.

Means to Solve the Problems

The present disclosure relates to a device for electrical measurement, and an electrical measurement apparatus including said device for electrical measurement shown hereafter.

(1) A device for electrical measurement, comprising:
a substrate on which are formed at least a sample separation channel and a sample migration channel, and a sample measuring unit;
wherein one end of the sample separation channel is formed to connect to one end of the sample migration channel; and
the sample measuring unit comprises a first measuring unit connected to the sample migration channel, and a second measuring unit connected to the sample migration channel from the reverse side to the first measuring unit.

(2) The device for electrical measurement of (1) above, wherein the first measuring unit and the second measuring unit are formed at asymmetrical positions flanking the sample migration channel.

(3) The device for electrical measurement of (1) above, wherein the sample measuring unit comprises a first measuring unit and a second measuring unit, the first measuring unit and the second measuring unit being formed as electrodes, and formed to cut across the sample migration channel.

(4) The device for electrical measurement of any of (1)-(3) above, wherein pillars are formed in the sample separation channel.

(5) The device for electrical measurement of any of (1)-(4) above, comprising a sample input channel connected to the other end of the sample separation channel, and a sample recovery channel connected to the other end of the sample migration channel.

(6) The device for electrical measurement of any of (1)-(5) above, wherein connected to the sample separation channel is a separated sample discharge channel for discharging separated and removed elements in the sample.

(7) The device for electrical measurement of any of (1)-(6) above, comprising a sample collecting apparatus for collecting samples.

(8) The device for electrical measurement of (7) above, wherein the sample collecting apparatus has an inclined sample collecting unit, and
a sample input hole formed on the top part of the inclined sample collecting unit, for inputting collected samples into the sample input channel.

(9) The device for electrical measurement of (8) above, wherein cones are formed on the inclined sample collecting unit.

(10) The device for electrical measurement of (8) or (9) above, wherein nanowires are formed on the sample collecting unit.

(11) An electrical measurement apparatus, comprising:
the device for electrical measurement of any of (1)-(10) above,
a drive circuit to make it possible to move the sample in the sample migration channel, and
a measuring circuit for applying voltage to the first measuring unit and the second measuring unit, and measuring the change in current when the sample moves in the sample migration circuit.

(12) The electrical measurement apparatus of (11) above, wherein the measuring circuit further comprises a variable resistor and a resistance element, it being possible to have a balanced state for the potential difference of the part sandwiched between the first measuring unit and the second measuring unit in the sample migration channel, and the potential difference of the resistance element.

(13) The electrical measurement apparatus of (11) or (12) above, wherein the measuring circuit measures the transient current and steady-state current changes.

(14) The electrical measurement apparatus of any of (11)-(13) above, further comprising a fluorescence microscope.

Advantageous Effects of the Invention (1) With the device for electrical measurement of the present disclosure, a sample migration channel in which a sample can flow is formed, and a first measuring unit connected to the sample migration channel and a second measuring unit connected to the sample migration channel from the reverse side to the first measuring unit are formed. Thus, with the electrical measurement apparatus using the device for electrical measurement of the present disclosure, the sample drive circuit and measuring circuit can be designed as separate circuits, and a high voltage can be set for the drive circuit to increase the detection sensitivity, so the transient current can be read accurately. Furthermore, when a variable resistor is incorporated in the measuring circuit, it is possible to read differences with the drive circuit and the measuring circuit in a balanced state, so the detection sensitivity can be further increased.

(2) With the electrical measurement apparatus of the present disclosure, by reading the transient current, the input/output timing of the sample to the sample migration channel can be accurately measured, and the surface charge and deformability of the sample can be measured from the passage rate.

(3) The device for electrical measurement of the present disclosure can be used placed horizontally, so by using combined with fluorescence microscope observation, more accurate analysis is possible.

(4) When the device for electrical measurement of the present disclosure has the sample separation channel formed before the sample migration channel, components not subject to analysis in the input sample can be separated and removed, making high sensitivity analysis possible.

(5) When sample collecting apparatus for collecting samples are formed, it is possible to collect harmful and hazardous substances floating in air or water, and to automatically analyze harmful and hazardous substances in one's surroundings.

DESCRIPTION OF THE PREFERRED EMBODIMENTS

The following is a detailed explanation of the device for electrical measurement and the electrical measurement apparatus of the present embodiment. First, in the present specification, "steady-state current" means ion current flowing based on the electrical resistance value of the drive circuit and the measuring circuit, and is current flowing when a sample is not introduced in the sample migration channel, with a constant value that does not change. Also, a "change in steady-state current" means the change in the ion current value obtained by large changes in the circuit resistance value when a sample is introduced in the sample migration channel, and the sample reaches the part sandwiched between the first measuring unit and the second measuring unit in the sample migration channel. Also, "transient current" means ion current that flows momentarily in the measuring circuit.

Figure 1:
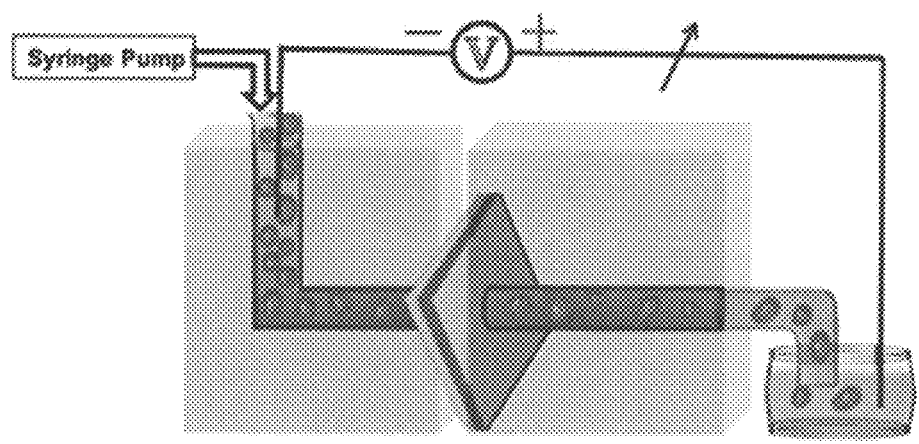
FIG. 1 shows the prior art of a method for measuring the size, number, etc., of a sample.
Figure 2:
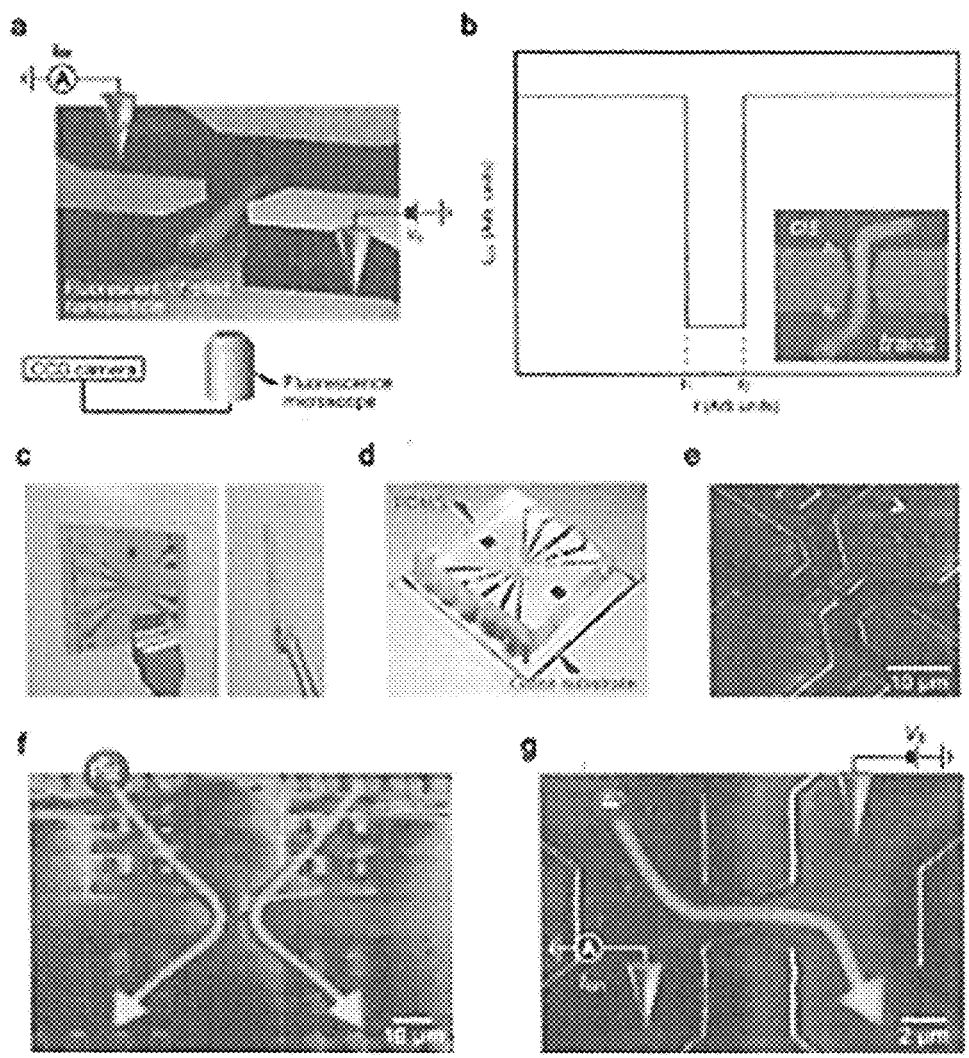
FIG. 2 shows FIG. 1 of Non-Patent Document 2.
Figure 3:
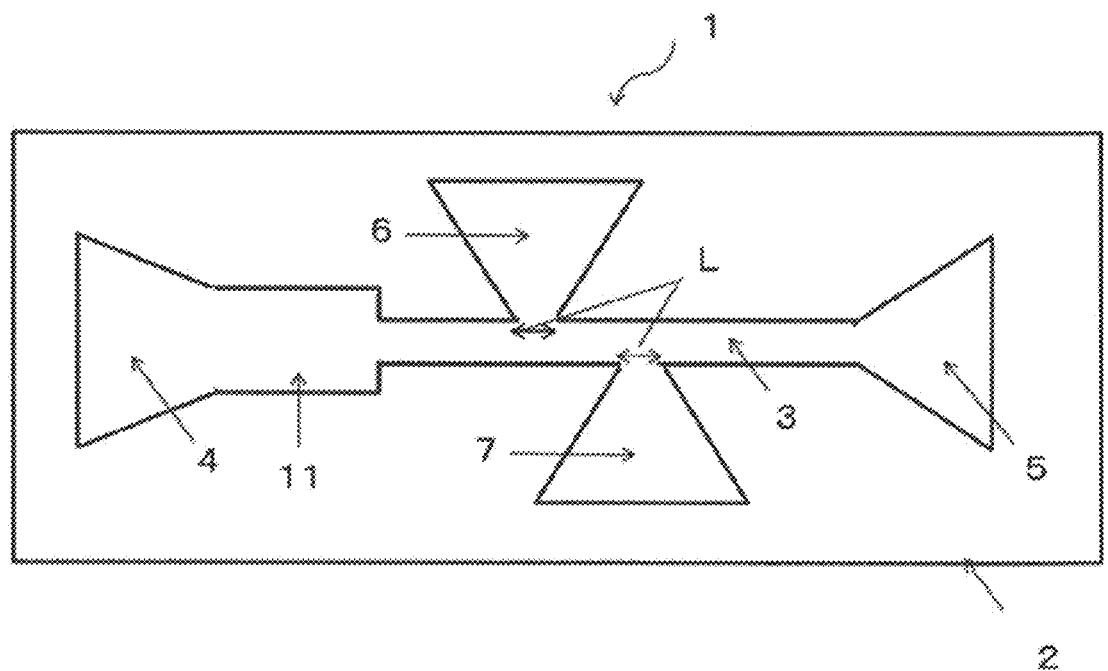
FIG. 3 is a diagram describing an overview of a device for electrical measurement 1 of the present embodiment.

FIG. 3 is a diagram describing an overview of the device for electrical measurement 1 of the present embodiment. The device for electrical measurement 1 shown in FIG. 3 includes: a substrate 2; a sample migration channel 3 formed on the substrate 2; a sample separation channel 11 connected to one end of the sample migration channel 3; a sample recovery channel 5 connected to the other end of the sample migration channel 3; a sample input channel 4 connected to the sample separation channel 11; as well a first measuring unit 6 connected to the sample migration channel 3, and a second measuring unit 7 connected to the sample migration channel 3 from the reverse side to the first measuring unit 6 (hereafter when channels formed on the substrate are consolidated, these may simply be noted as "channels"). Also, a sample measuring unit is formed by the first measuring unit 6 and the second measuring unit 7.

The width and depth of the sample migration channel 3 is not particularly limited as long as they are larger than the size of the sample, but to improve the measurement sensitivity, it is preferable so suitably adjust to not be too much larger than the size of the sample. For example, the diameter of PM2.5 in air is approximately 2.5 µm, so it is acceptable if the width and depth of the sample migration channel 3 is approximately 3 µm. Also, the diameter of cedar pollen is said to be approximately 20 to 40 µm, and of cypress pollen to be approximately 28 µm to 45 µm, so the width and depth are acceptable at approximately 50 µm. As shall be apparent, the abovementioned numerical values are guidelines, and when the sample is even larger, the width and depth can be made larger according to the size of the sample, such as 100 µm, 150 µm, 200 µm, etc. For the lower limit of the width and depth, with the current fine processing technology, the limit is approximately 4 nm, but with advances in technology, this can be made even smaller. The device for electrical measurement 1 of the present embodiment can be designed to be different from the fine pores of the prior art, with the sample migration channel 3 made long, and it is possible to produce a stretched state of the sample inside the sample migration channel 3 and measure biomolecules of nucleic acid, protein, etc.

For the sample input channel 4 and the sample recovery channel 5, size and shape are not particularly limited provided the size allows electrodes of the sample drive circuit to be input, and liquid containing the sample (hereafter, liquid containing the sample may be noted as "sample liquid") can be input and recovered, but it is preferable that the depth be made the same as that of the sample migration channel 3. To make it possible for the sample to flow into the sample separation channel 11 efficiently, the sample input channel 4 can have a tapered shape with the width narrowing facing the sample separation channel 15. The sample recovery channel 5 can also have a tapered shape with the width expanding from the sample migration circuit 3.

The first measuring unit 6 and the second measuring unit 7 configure the measuring circuit, and are used to measure steady-state current changes and transient current (hereafter, measuring steady-state current changes and transient current may be noted as "measurement of current changes"). The first measuring unit 6 and the second measuring unit 7 can be formed by forming a channel connected to the sample migration channel 3, and inputting electrodes inside the channel. Configuration is also possible with the electrodes contacting the sample migration channel 3.

When the first measuring unit 6 and the second measuring unit 7 are formed by channels, the size and shape of the channels are not particularly limited as long as the size allows the sample measuring circuit electrodes to be input, but to increase the measurement sensitivity, it is preferable to lower the resistance. The resistance value of the channel filled with sample liquid is a value of the product of the sample liquid resistivity and the channel length, divided by the cross section area of the channel. Therefore, the area becomes larger as the channel width increases, and the resistance can be lowered. Therefore, the width of the first measuring unit 6 and the second measuring unit 7 is preferably longer than the length L of the part connected with the sample migration channel 3 in accordance with separation from the sample migration channel 3. The shape of the first measuring unit 6 and the second measuring unit 7 can be the same or different, but if the shape of the first measuring unit 6 and the second measuring unit 7 is different, the signals obtained with measurement will also be asymmetrical. Therefore, when doing higher precision measurement of the shape, etc., of items from the measured signal, it is preferable to have the same shape for the first measuring unit 6 and the second measuring unit 7.

Figure 4:
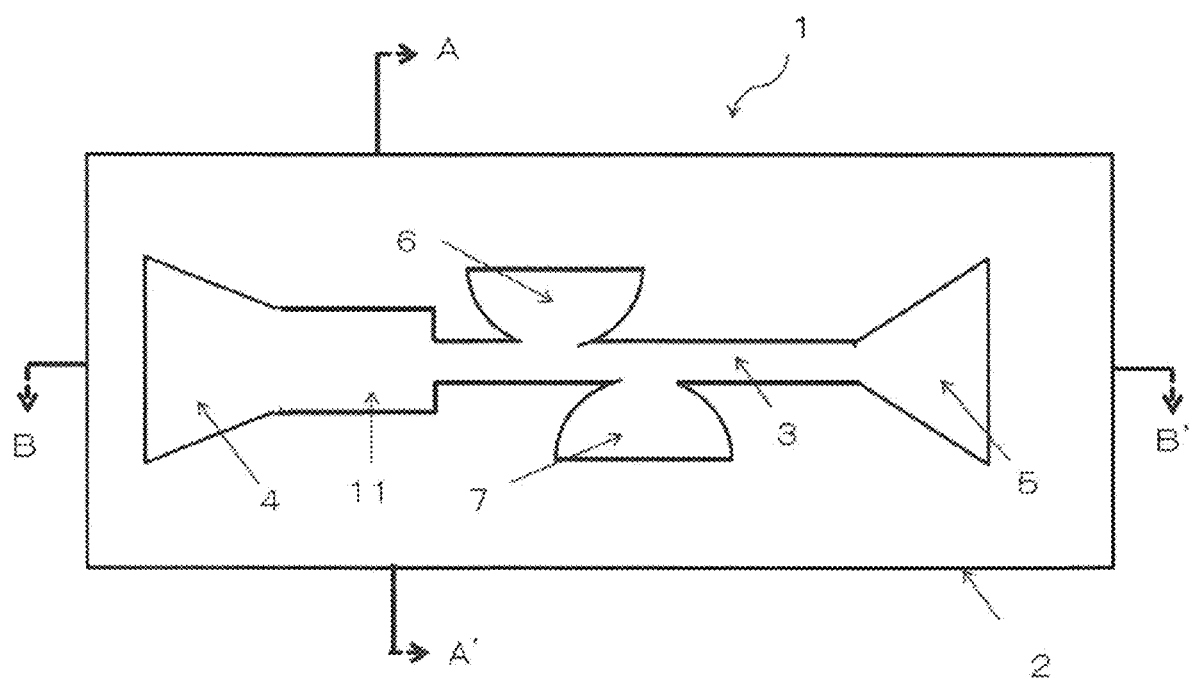
FIG. 4 shows another embodiment of the device for electrical measurement 1 of the present embodiment.

In FIG. 3, by making the first measuring unit 6 and the second measuring unit 7 be approximately trapezoidal, the width of the first measuring unit 6 and the second measuring unit 7 is longer than L, but the shape is not particularly limited provided it is a shape for which the width of the first measuring unit 6 and the second measuring unit 7 becomes longer as it separates from the sample migration channel 3. For example, FIG. 4 shows another embodiment of the device for electrical measurement 1 of the present embodiment, and as shown in FIG. 4, this can also be made longer as it separates from the sample migration channel 3 by using a semicircular shape.

The depth of the first measuring unit 6 and the second measuring unit 7 can be the same as the depth of the sample migration channel 3. Also, since sensitivity is better the shorter that length L is, it should be made short to the degree that production is possible with fine processing technology. On the other hand, when the length L is too long, there is the risk of the sample flowing into the first measuring unit 6 or the second measuring unit 7 from the sample migration channel 3, so it is preferable that the length L be shorter than the width of the sample migration channel 3, and more preferable that it be shorter than the size of the sample subject to measurement.

Figure 5:
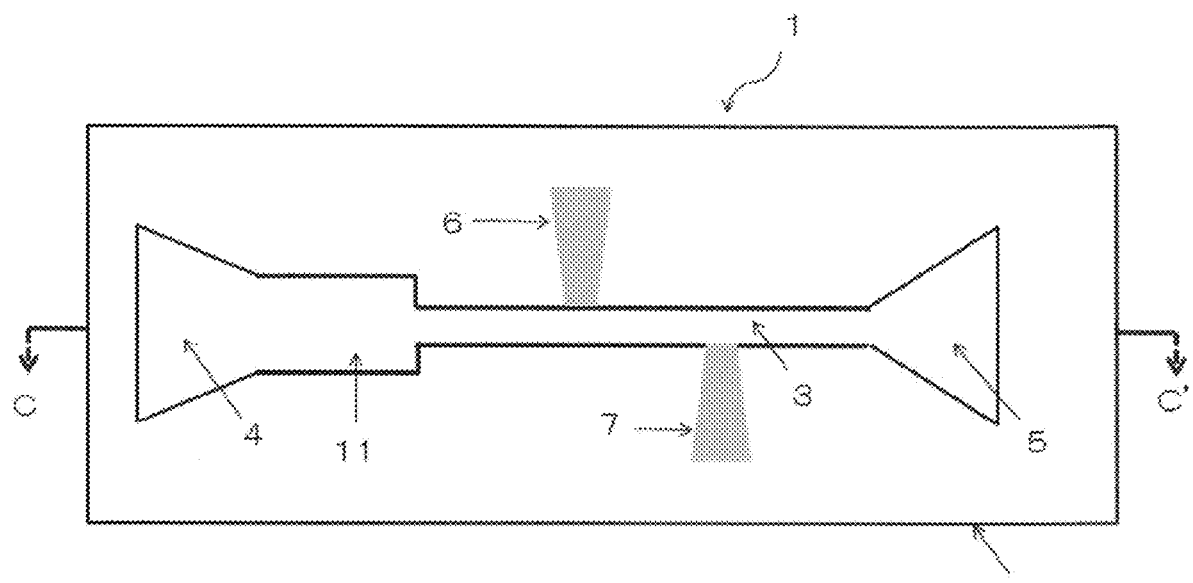
FIG. 5 is a diagram describing an overview of the device for electrical measurement 1 with a first measuring unit 6 and a second measuring unit 7 formed with electrodes.

FIG. 5 is a diagram describing an overview of the device for electrical measurement 1 with the first measuring unit 6 and the second measuring unit 7 formed with electrodes. When forming the first measuring unit 6 and the second measuring unit 7 with electrodes, it is not necessary to form a channel, and after the sample migration channel 3 is formed, an electrically conductive material can be coated up to the position in contact with the sample migration channel 3. When using the device for electrical measurement 1, since a lid of glass, etc. (seal member) is put on, inside the sample migration channel 3 is filled with the sample liquid. Thus, it is possible to make the sample liquid conductive even if electrodes are formed on the substrate 2. With the present embodiment, regardless of the arrangement, the members that form the channel are noted as the substrate, and the members that do not form the channel are noted as the seal member.

As the electrode material, known electrically conductive metals such as aluminum, copper, platinum, gold, silver, titanium, etc., can be used. Also, the electrodes can be produced by masking the substrate 2 and doing vapor deposition of the material. Compared to the mode of forming the first measuring unit 6 and the second measuring unit 7 with channels and inserting the electrodes, it is possible to have less resistance by forming the first measuring unit 6 and the second measuring unit 7 with electrodes. Thus, it is possible to have less voltage applied to the sample migration channel 3. The length of the connecting part between the sample migration channel 3 and the electrodes can be handled the same as noted above. It is also preferable to make the shape of the facing electrodes be the same. In the case of electrodes as noted above, since it is possible to have less resistance, the width of the first measuring unit 6 and the second measuring unit 7 can be longer as it separates from the sample migration channel 3 as shown in FIG. 3 and FIG. 4, but it can also be the same width such as with a rectangle, etc.

Figure 6:
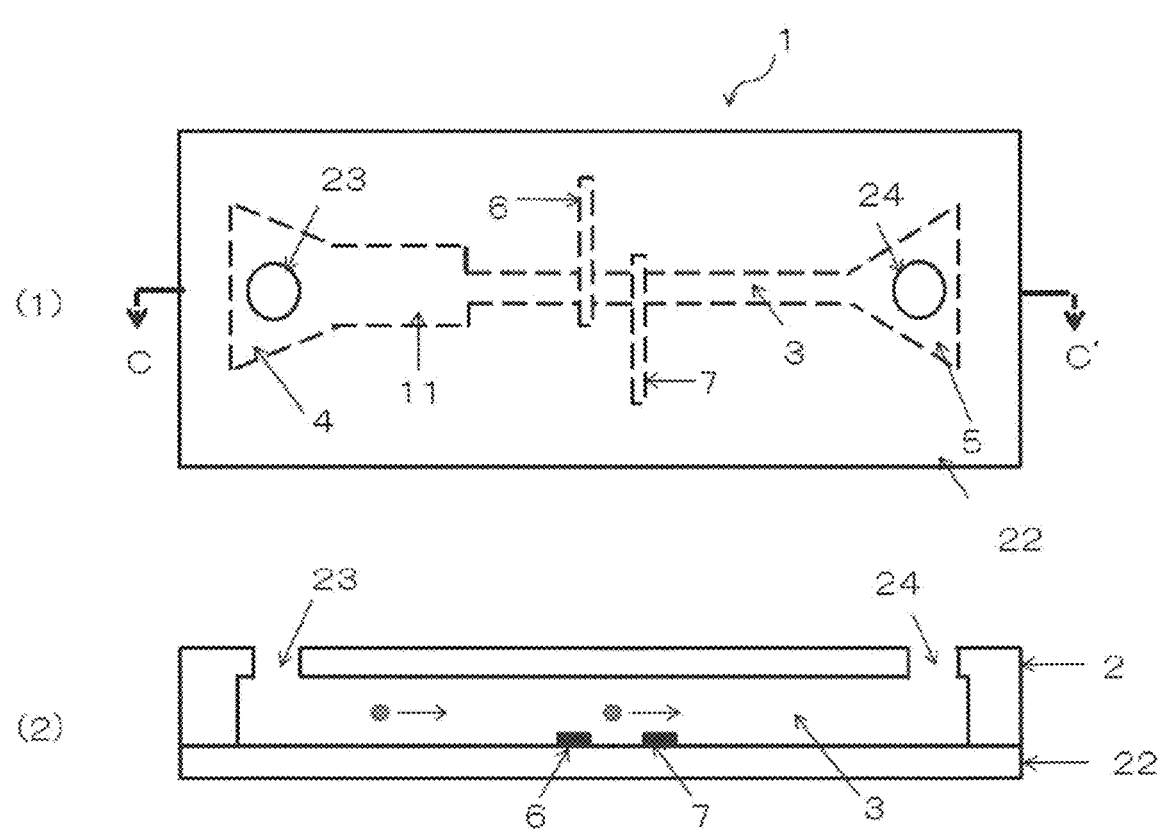
FIG. 6 includes diagrams describing another embodiment of the device for electrical measurement 1 with the first measuring unit 6 and the second measuring unit 7 formed with electrodes, with FIG. 6(1) being a top view, and FIG. 6(2) being a C-C' cross section diagram.

With the embodiments shown in FIG. 3 to FIG. 5, the sample measuring unit includes the first measuring unit 6, and the second measuring unit 7 connected to the sample migration channel 3 from the reverse side to the first measuring unit 6, but it is also possible for the first measuring unit 6 and the second measuring unit 7 to be formed using an electrode, and to be formed cutting across the sample migration channel 3. FIG. 6 is a diagram describing an embodiment of the device for electrical measurement 1 in which the first measuring unit 6 and the second measuring unit 7 are formed with electrodes, and formed to cut across the sample migration channel 3, with FIG. 6(1) being a top view, and FIG. 6(2) representing a cross section diagram across C-C'. With the embodiment shown in FIG. 6, electrodes (the first measuring unit 6 and the second measuring unit 7) are formed on the seal material 22, and formed on the substrate 2 are the sample migration channel 3, the sample input channel 4, the sample recovery channel 5, and the sample separation channel 11, etc. Also, on the substrate 2, a sample input hole 23 for inputting the samples to the sample input channel 4, and a sample recovery hole 24 for recovering the sample from the sample recovery channel 5 are formed to pierce through the substrate 2. With the embodiment shown in FIG. 6, when the substrate 2 and the seal member 22 are combined, the electrodes (the first measuring unit 6 and the second measuring unit 7) separate in the direction in which the sample of the sample migration channel 3 flows, and are formed to cut across the sample migration channel 3. As shown in FIG. 6(2), the device for electrical measurement 1 of this embodiment can measure transient current when the sample flows between the first measuring unit 6 and the second measuring unit 7.

Figure 7:
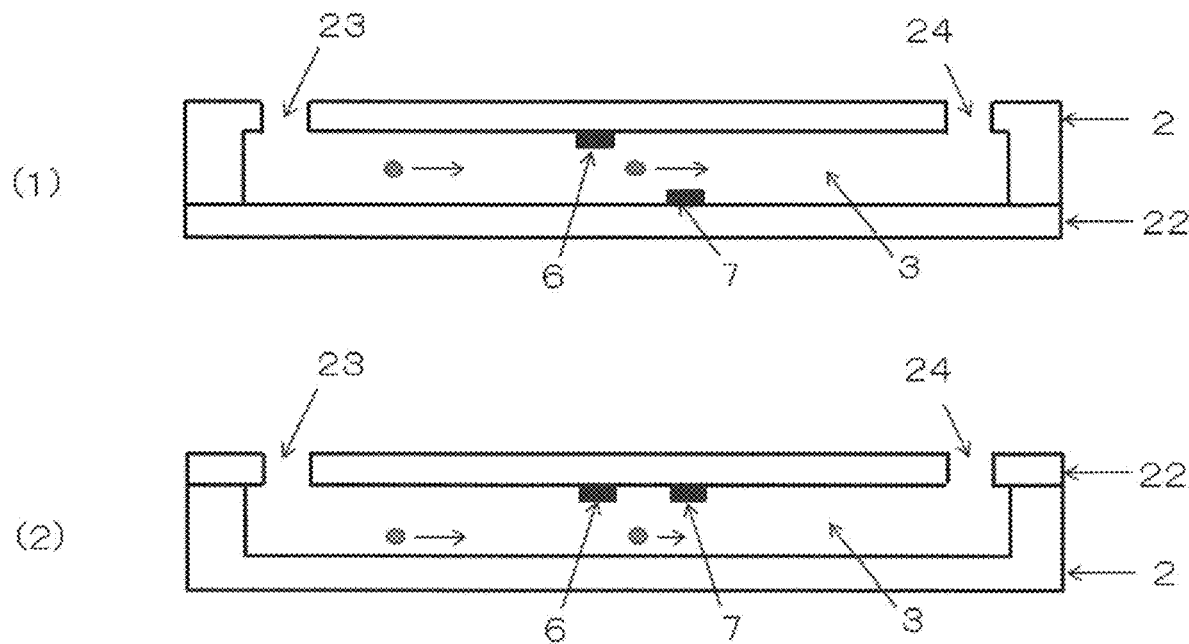
FIGS. 7(1) and (2) are cross section diagrams describing another embodiment of the device for electrical measurement 1 with the first measuring unit 6 and the second measuring unit 7 formed with electrodes.

FIG. 7 is a cross section diagram describing another embodiment of the device for electrical measurement 1 for which the first measuring unit 6 and the second measuring unit 7 are formed with electrodes, and are formed to cut across the sample migration channel 3. The embodiment shown in FIG. 7(1) is the same as the embodiment shown in FIG. 6 except for one or the other of the first measuring unit 6 and the second measuring unit 7 being formed on the seal material 22 and the other on the substrate 2, and the electrodes being formed so as to sandwich the sample migration channel 3. When the substrate 2 and the seal material 22 are combined, the first measuring unit 6 and the second measuring unit 7 can be formed at symmetrical positions flanking the sample migration channel 3, but it is preferable that they be formed at asymmetrical positions flanking the sample migration channel 3.

FIG. 7(2) is a cross section diagram describing another embodiment of the device for electrical measurement 1 with the first measuring unit 6 and the second measuring unit 7 formed with electrodes, and formed to cut across the sample migration channel 3. The embodiment shown in FIG. 7(2), the same as with the embodiments shown in FIG. 3 to FIG. 5, has the sample migration channel 3, the sample input channel 4, the sample recovery channel 5, the sample separation channel 11, etc., formed on the substrate 2 side, the first measuring unit 6 and the second measuring unit 7 formed on the seal material 22 separating in the direction in which the sample of the sample migration channel 3 flows, and to cut across the sample migration channel 3, and has the sample input hole 23 and the sample recovery hole 24 formed.

Other than being formed to cut across the sample migration channel 3, the electrodes of the embodiment shown in FIG. 6 and FIG. 7 can be formed with the same material as the embodiment shown in FIG. 5.

The sample separation channel 11 is formed between the sample input channel 4 and the sample migration channel 3, and is formed to remove items not subject to analysis in the sample liquid. For example, large size microparticles such as PM10, etc., in the atmosphere are removed and PM2.5 is analyzed, microbes etc. in the sample are removed and only the effluent is analyzed, specific components such as protein, etc. in the biological sample are removed and the nucleic acid is analyzed, etc., and this is not particularly limited provided that items not subject to analysis can be removed from the input sample. For example, when removing large size particles in the sample, examples include forming a size separation filter on the sample separation channel 11, forming a filter by forming nanowires in a densely packed state, forming pillars for performing size separation using the flow of liquid, etc. Also, when removing specific components such as protein, etc., in the sample, for example, a filter on which antibodies are supported, nanowires, pillars, etc. can be formed on the sample separation channel 11.

Items available on the market can be used for the sample separation filter.

For nanowires, particles for nanowire formation or a catalyst are coated on the sample separation channel 11, and the nanowire can be grown using a known method. As the particles for nanowire formation, an example is ZnO. The nanowire using ZnO microparticles can be produced using the hydrothermal synthesis method. In specific terms, first, ZnO particles are coated on the sample separation channel 11.

Next, by immersing the heated substrate in a precursor solution for which zinc nitrate hexahydrate ($Zn(NO_3)_2 \cdot 6H_2O$) and hexamethylene tetramine ($C_6H_{12}N_4$) are dissolved in deionized water, it is possible to grow ZnO nanowire.

As the catalyst for producing a nanowire, examples include gold, platinum, aluminum, copper, iron, cobalt, silver, tin, indium, zinc, gallium, chrome, titanium, etc. Nanowire using the catalyst can be produced using the following procedure.

(a) The catalyst is deposited on the sample separation channel 11.

(b) Using a material such as $SiO_2$, $Li_2O$, $MgO$, $Al_2O_3$, $CaO$, $TiO_2$, $Mn_2O_3$, $Fe_2O_3$, $CoO$, $NiO$, $CuO$, $ZnO$, $Ga_2O_3$, $SrO$, $In_2O_3$, $SnO_2$, $Sm_2O_3$, $EuO$, etc., core nanowire is formed using a physical vapor deposition method such as pulse laser deposition, VLS (Vapor-Liquid-Solid) method, etc.

(c) Using $SiO_2$, $TiO_2$, etc., which are materials for which crushed and extracted nucleic acid is not easily absorbed using electrostatic interaction, using a typical vapor deposition method such as sputtering, electron beam (EB) vapor deposition, physical vapor deposition (PVD), atomic layer deposition (ALD), etc., a coating layer is formed surrounding the core nanowire. The nanowire produced using the catalyst can be nanowire that does not have a branched chain, and can also be a nanowire that does have a branched chain.

Figure 8:
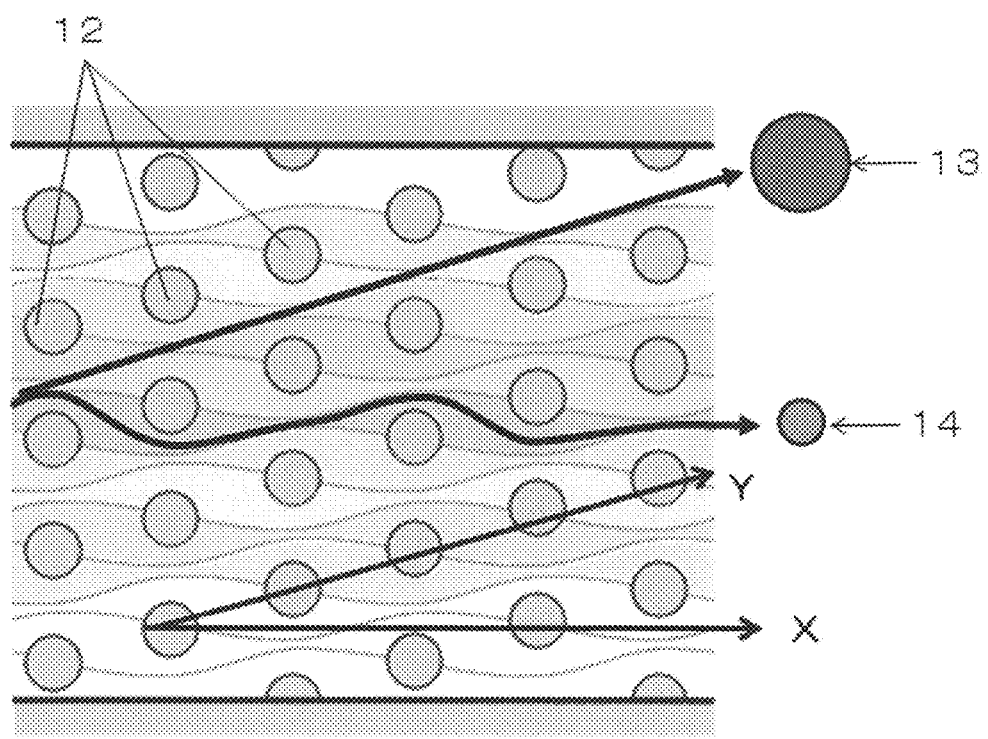
FIG. 8 is a diagram describing the principle of separating microparticles of different sizes by the action of fluid flowing between pillars 12.

Pillars can be produced simultaneously with other channels such as the sample input channel 4, etc., using a manufacturing method that uses etching described later. When forming pillars by etching, it is possible to control the pillar diameter and arrangement, etc. FIG. 8 is a diagram describing the principle of separating microparticles of different sizes by the effect of fluid flowing between the pillars 12. When the pillars 12 are provided in a prescribed angle Y direction to the channel direction X, large particles 13 flow in the Y direction (wall surface direction of the sample separation channel 11). Meanwhile, small particles 14 flow along between the pillars 12, making it possible to separate microparticles of different sizes. The diameter of the pillars 12, and the gap between pillars 12 and the angle to the channel direction X can be set as appropriate according to the size of the microparticles being separated. Also, the cross section shape of the pillars 12 can be adjusted as appropriate to be circular, elliptical, triangular, etc. The optimal design of the pillars 12 can be designed by referring to J. McGrath et al., "Deterministic lateral displacement for particle separation: a review," Lab on a Chip, Vol. 14, pp. 4139-4157 (2014), etc., for example.

Figure 9:
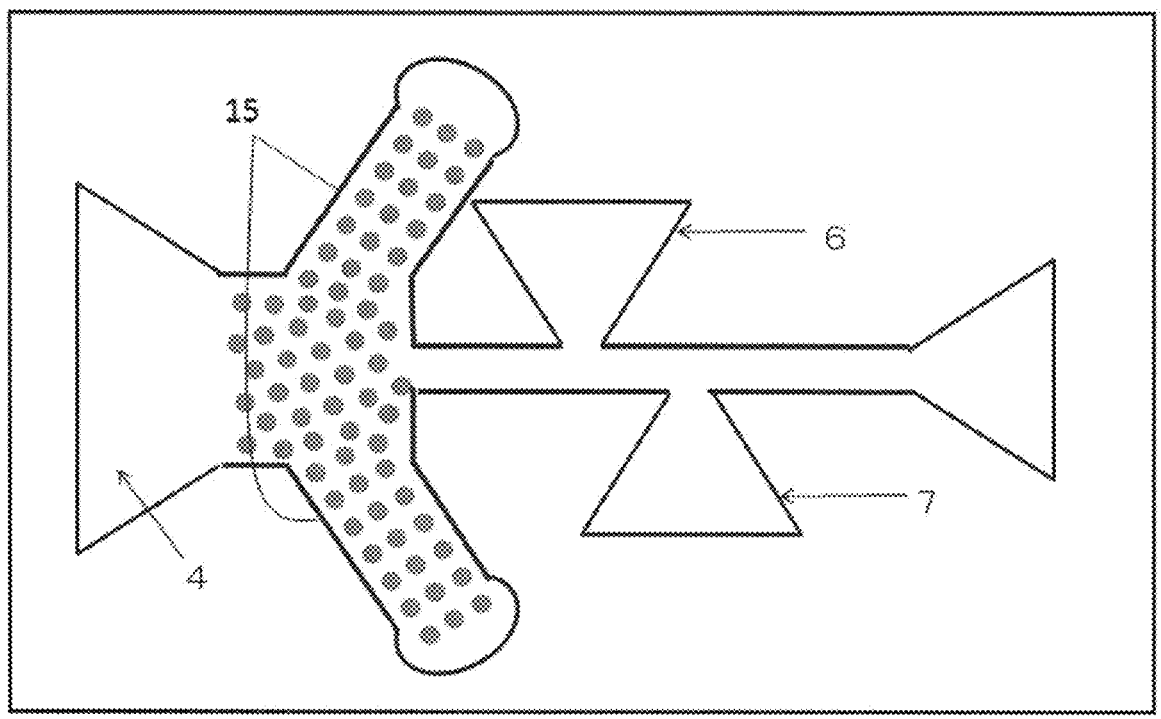
FIG. 9 is a diagram showing an overview of the device for electrical measurement 1 with a separated sample discharge channel 15 provided in a sample separation channel 11.

When separating microparticles using pillars 12, as shown in FIG. 9, it is also possible to provide a separated sample discharge channel 15 in the sample separation channel 11. The separated large samples 13 can pass through the separated sample discharge channel 15 and be discharged, so their entry inside the sample migration channel 3 can be prevented, making it possible to reduce noise.

Figure 10:
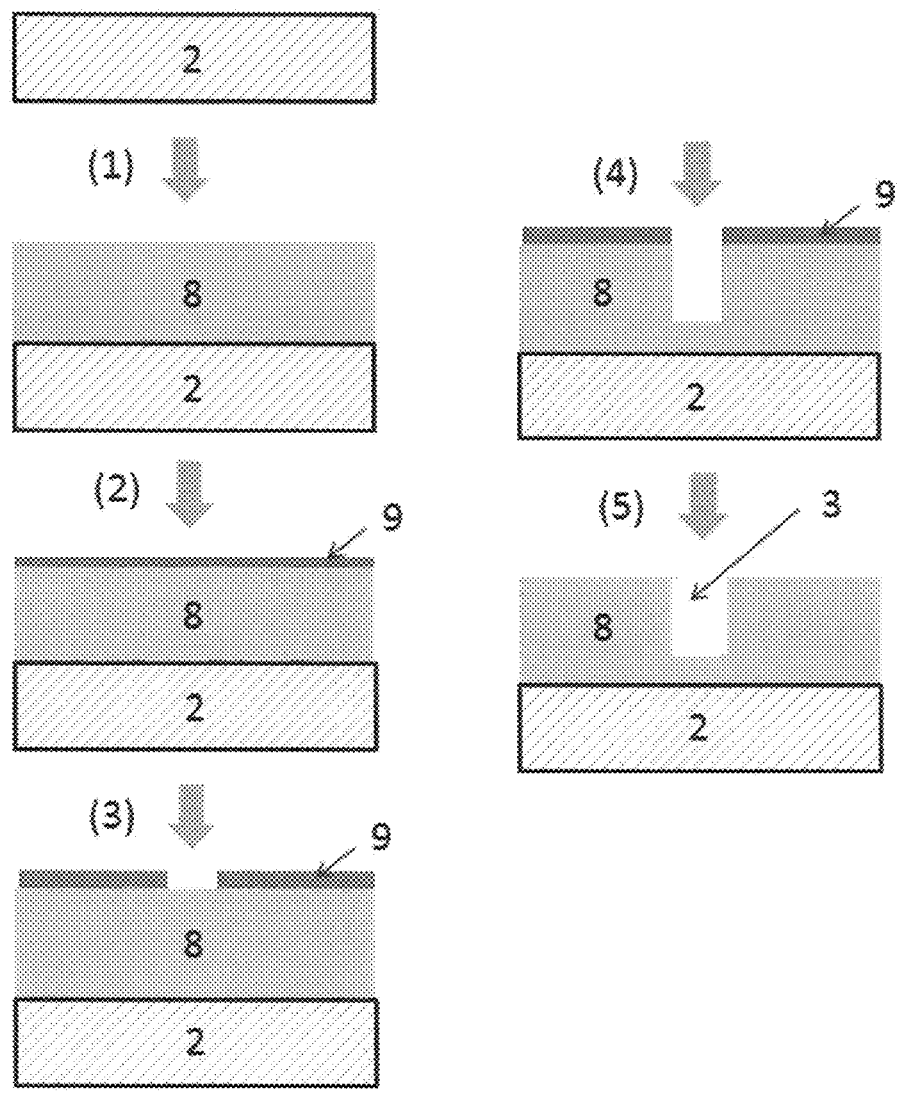
FIG. 10 is a cross section diagram across A-A' in FIG. 4, and shows an example of a manufacturing process for the device for electrical measurement 1.

The device for electrical measurement 1 can be manufactured using fine processing technology. FIG. 10 is a cross section diagram across A-A' in FIG. 4, and shows an example of the manufacturing steps of the device for electrical measurement 1.

(1) An etchable material 8 is coated using chemical vapor deposition on the substrate 2.

(2) A positive photoresist 9 is coated using a spin coater.

(3) To irradiate light on locations at which the channels are formed, exposure and developing processes are done using a photomask, and the positive photoresist 9 of the part forming the channels is removed.

(4) The material 8 at the locations for forming channels is etched, and channels are formed on the substrate 2.

(5) The positive photoresist 9 is removed, and filters or nanowires are formed on the sample separation channel 11 part.

The substrate 2 is not particularly limited provided it is a material typically used in the field of semiconductor manufacturing technology. As the material of the substrate 2, examples include silica glass, Si, Ge, Se, Te, GaAs, GaP, GaN, InSb, InP, etc.

The positive photoresist 9 is not limited provided it is an item typically used in the field semiconductor manufacturing particularly, such as TSMR V50, PMER, etc. It is also possible to use a negative photoresist instead of a positive type, and this is not particularly limited provided it is an item typically used in the semiconductor manufacturing field, such as SU-8, KMPR, etc. The photoresist removal liquid is not particularly limited provided it is a removal liquid typically used in the semiconductor field, such as dimethylformamide, acetone, etc.

The material 8 for depositing on the substrate 2 to form channels and other than channels is not particularly limited provided it is an insulating material, and examples include $SiO_2$, $Si_3N_4$, BPSG, SiON, etc. With the manufacturing steps shown in FIG. 10, the channel is formed using the etchable material 8, but as the material 8, it is also possible to use a photosensitive resin such as the abovementioned positive photoresist, negative photoresist, etc. When using a photosensitive resin, the photosensitive resin is coated on the substrate 2, and using a photomask of a shape by which a channel can be formed, the channel can be formed with the photosensitive resin by exposure and development.

Figure 11:
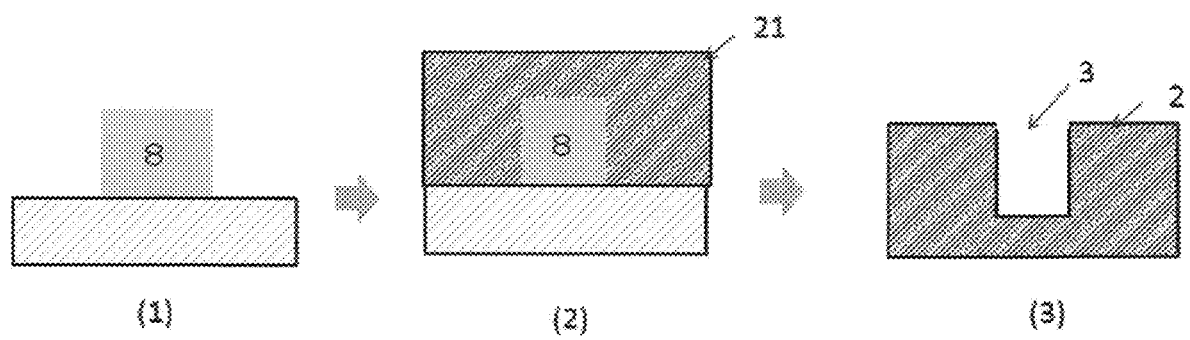
FIG. 11 is a diagram showing another manufacturing process for the device for electrical measurement 1 of the present embodiment.

FIG. 11 is a diagram showing other manufacturing steps of the device for electrical measurement 1 of the present embodiment. The manufacturing steps shown in FIG. 10 form a channel by etching, but with the manufacturing steps shown in FIG. 11, the device for electrical measurement 1 can be produced by transferring a casting mold.

(1) By changing the shape of the photomask, a convex part 8 that forms the channel after transfer is formed on the substrate, and the casting mold is produced.

(2) The casting mold is transferred to the material 21 for transfer.

(3) The casting mold is peeled off, and filters and nanowires are formed on the sample separation channel 11 part, producing the substrate 2.

Examples of the material 21 for transferring the casting mold include insulating materials such as plastics made of polydimethyl siloxane (PDMS), polymethyl methacrylate (PMMA), polycarbonate (PC), hard polyethylene, etc. The transferred and produced device for electrical measurement 1 can also be pasted to an auxiliary substrate of glass, plastic, etc. to improve handling convenience.

Figure 12:
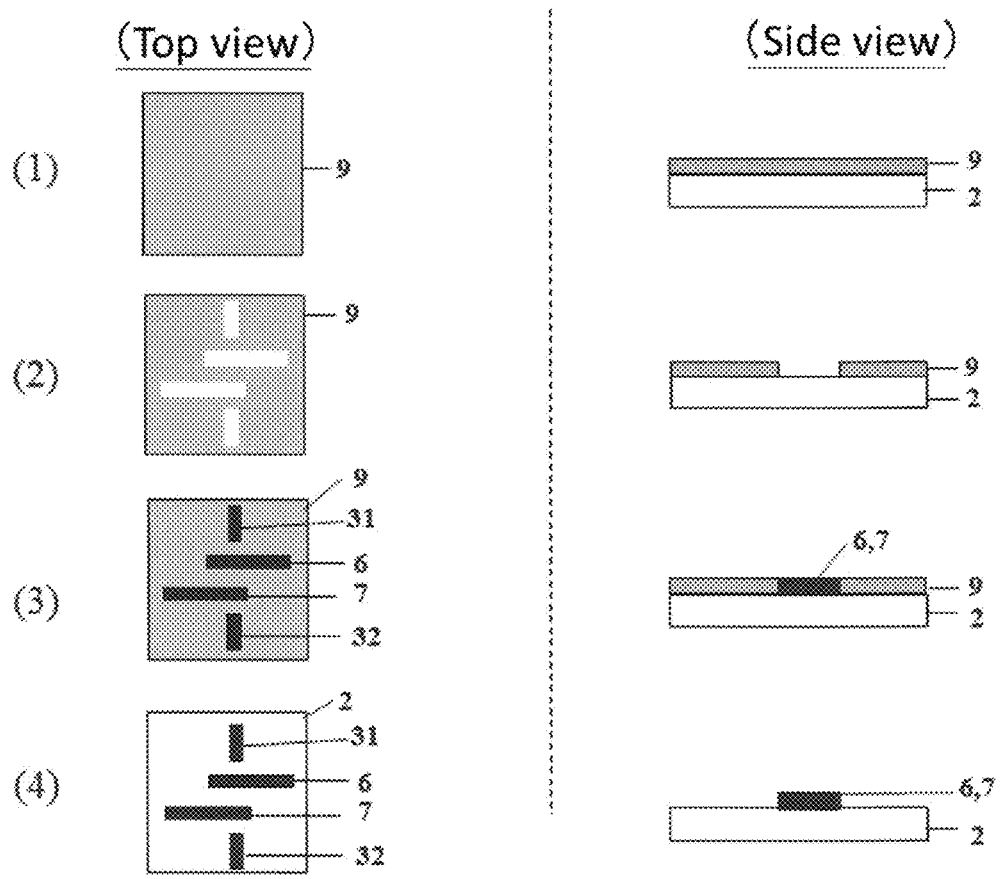
FIG. 12 is a diagram showing the procedure for forming electrodes (first measuring unit 6 and/or second measuring unit 7) on a seal material 22.

Also, in the case of the embodiment shown in FIG. 6 and FIG. 7(1), first, using the procedure shown in FIG. 12, electrodes (first measuring unit 6 and/or second measuring unit 7) are formed on the seal material 22.

(1) The positive photoresist 9 is coated on the seal material 22 using a spin coater.

(2) To irradiate light on the locations for forming the first measuring unit 6 and/or the second measuring unit 7, exposure and development processes are done using a photomask, and the positive photoresist 9 of the part for forming the first measuring unit 6 and/or the second measuring unit 7 is removed. In addition to the first measuring unit 6 and/or the second measuring unit 7, it is also possible to form electrodes 31, 32 as necessary to configure the sample drive circuit described later.

(3) Material for forming electrodes is deposited on the part at which the positive photoresist 9 was removed in (2) noted above.

(4) The positive photoresist 9 is removed.

Next, the substrate 2 is produced. Other than using a photomask of a shape by which it is possible to form the sample migration channel 3, the sample input channel 4, the sample recovery channel 5, and the sample separation channel 11, the substrate 2 can be produced using the same procedure and material as in FIG. 11 noted above. Furthermore, as necessary, the sample input hole 23 and the sample recovery hole 24 can be formed by machining, etc. It is also possible to produce the device for electrical measurement 1 by adhering the substrate 2 and the seal material 22 to be fluid-tight.

With the embodiment shown in FIG. 7(1), it is necessary to form the electrodes (first measuring unit 6 and/or second measuring unit 7) on the substrate 2 (material 21 for transferring the casting mold) on which channels, etc., are formed. When using the material 21 that transfers the casting mold such as PDMS, PMMA, PC, etc. as the substrate 2, the electrodes can be formed using the method noted in "Ikjoo Byun et. al., J. Micromech. Microeng., 23, 085016, 2013."

Also, with the embodiment shown in FIG. 7(2), the channels are formed at the substrate 2 side, so the electrodes should be formed on the seal material 22. When using glass as the seal material 22, the electrodes should be formed using the procedure shown in FIG. 12, and when using PDMS, PMMA, PC, etc., the electrodes should be formed using the method noted in the abovementioned document.

When measuring using the device for electrical measurement 1 of the present embodiment, when observing using a fluorescence microscope, it is preferable that the substrate 2, the material 8, the material 21 for transferring the casting mold, the auxiliary substrate, and the seal material 22 be formed using a light transmitting material.

Also, the device for electrical measurement 1 can also be formed as an integrated unit with the photomask on which the various channel and pillar arrangement is designed made to cover the substrate 2 made of silicon, etc., using a method such as plasma etching, etc.

The device for electrical measurement 1 can also undergo hydrophilic treatment to make the sample liquid flow more easily. Examples of the hydrophilic treatment method include plasma treatment, surfactant treatment, PVP (polyvinyl pyrrolidone) treatment, a photo catalyst, etc., and by doing plasma treatment for 10 to 30 seconds on the surface on which the channels of the device for electrical measurement 1 are formed, for example, it possible to introduce a hydroxyl group to the surface.

Figure 13:
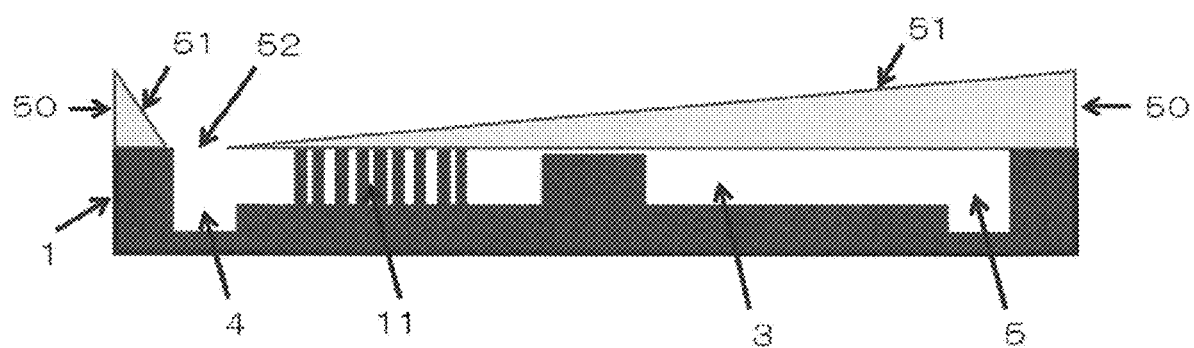
FIG. 13 is a cross section diagram across B-B' shown in FIG. 4 when an example of a sample collecting apparatus 50 is provided in the device for electrical measurement 1.

The device for electrical measurement 1 of the present embodiment can also be provided with sample collecting apparatus for collecting samples. FIG. 13 is a cross section diagram across B-B' when a sample collecting apparatus 50 is provided on the device for electrical measurement 1 shown in FIG. 4. The sample collecting apparatus 50 is not particularly limited provided it is possible to input samples contained in the atmosphere or water into the sample input channel 4. Shown in FIG. 13 is a cone shaped sample collecting apparatus 50 on which are formed an inclined sample collecting unit 51, and a sample input hole 52 for inputting collected samples into the sample input channel 4.

The sample collecting apparatus 50 can be produced using an insulating material such as a plastic, etc., made of polydimethyl siloxane (PDMS), polymethyl methacrylate (PMMA), polycarbonate (PC), hard polyethylene, etc. Examples of the production method include machining or 3D printing. The produced sample collecting apparatus 50 can also undergo hydrophilic treatment or hydrophobic treatment as necessary. For example, when analyzing a sample contained in water such a rain or waste water, etc., it is possible to make water flow more easily by doing hydrophobic treatment at least on the inclined sample collecting unit 51. Conversely, when collecting moisture contained in the atmosphere, when analyzing samples contained in the collected moisture, to make collecting of the moisture in the atmosphere easier, hydrophilic treatment can be done on the sample collecting unit 51.

Examples of hydrophobic treatment include fluorine treatment, plasma treatment, plasma polymerization, surface chemical modification, graft polymerization of a hydrophobic compound on the surface, coating of a hydrophobic polymer, a metal oxide film (using ALD), etc. Also, the hydrophilic treatment can be performed in the same manner as the abovementioned plasma treatment, surfactant treatment, PVP (polyvinyl pyrrolidone) treatment, metal oxide film, photocatalyst, etc. In all cases, the treatment can be performed using a known method.

Figure 14:
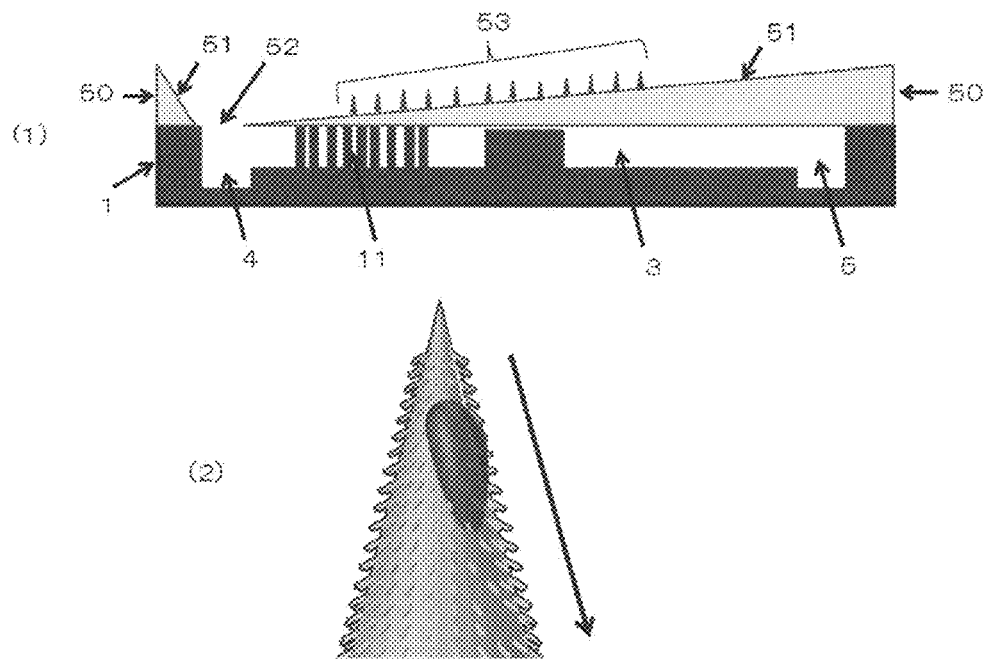
FIG. 14(1) shows an example of cones 53 formed on a sample collecting unit 51, and FIG. 14(2) shows an example of the nanowire density increasing toward the top part of the cone 53.

When collecting samples in air as the sample, by increasing the surface area of the sample collecting unit 51, collecting moisture in air becomes easier. FIG. 14(1) shows an example of the cones 53 formed on the sample collecting unit 51. The cones 53 are not particularly limited provided they are formed in a pointy shape from the surface of the sample collecting unit 51, such as a round cone, or a polygonal pyramid such as a triangular pyramid, quadrangular pyramid, etc. The moisture adsorbed on the cones 53 flows to the sample collecting unit 51 by gravity. When the cones 53 are formed randomly on the sample collecting unit 51 surface, it is difficult for the collected moisture to flow smoothly on the sample collecting unit 51. Therefore, it is preferable to form the cones 53 systematically, an example including a hexagonal close-packed arrangement, etc. The sample collecting apparatus 50 shown in FIG. 14(1) can be produced using a 3D printer. Instead of the cones 53, it is also possible to increase the surface area of the sample collecting unit 51 by forming nanowires on the sample collecting unit 51 using the method noted above.

Furthermore, after forming the cones 53 shown in FIG. 14(1), nanowires can be formed on the cones 53 and the sample collecting unit 51. When forming nanowires on the cones 53 as well, as shown in FIG. 14(2), it is preferable to increase the density of the nanowires the closer they approach the top part of the cones 53. When the density of the nanowires of the top part is increased, using the surface energy difference+the Laplace pressure difference, it is possible to flow the moisture collected by the cones 53 to the sample collecting unit 51 (arrow direction). With the embodiment shown in FIG. 14(2), nanowires can be grown by coating ZnO which is microparticles for forming nanowires. By having uniform ZnO growth, it is possible to increase the density of the nanowires the closer they approach to the top part of the cones 53.

Figure 15:
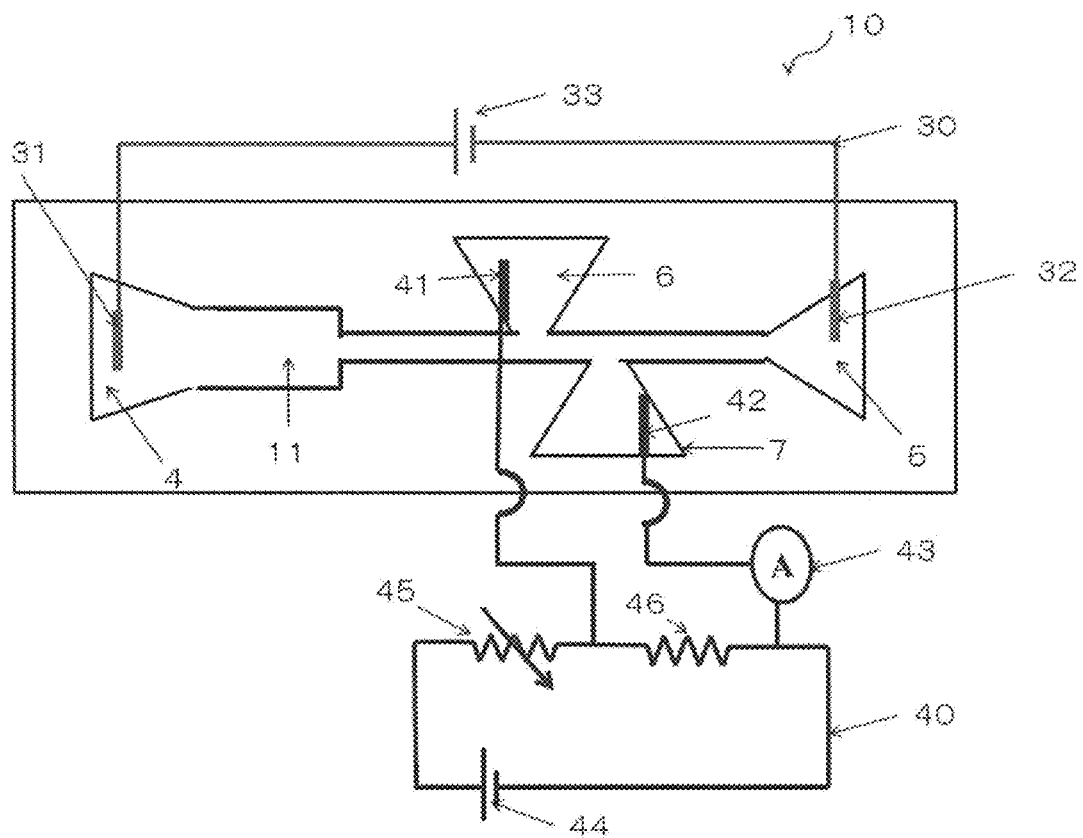
FIG. 15 is a diagram showing an overview of an electrical measurement apparatus 10 that uses the device for electrical measurement 1 of the present embodiment.

FIG. 15 is a diagram showing an overview of the electrical measurement apparatus 10 that uses the device for electrical measurement 1 of the present embodiment. The example shown in FIG. 14 is diagram describing an embodiment in which channels are formed as the first measuring unit 6 and the second measuring unit 7, and electrodes are inserted in the channels. In addition to the device for electrical measurement 1, the electrical measurement apparatus 10 includes a drive circuit 30 and a measurement circuit 40.

The drive circuit 30 includes a first electrode 31 inserted in the sample input channel 4 and a second electrode 32 inserted in the sample recovery channel 5, and a voltage application means 33. The first electrode 31 and the second electrode 32 are not particularly restricted provided they are a material that electricity passes through, and for example, known electrically conductive metals such as aluminum, copper, platinum, gold, silver, titanium, etc., can be used. With the example shown in FIG. 15, the first electrode 31 is inserted in the sample input channel 4, and the second electrode 32 is inserted in the recovery channel 5, but the first electrode 31 and the second electrode 32 can be formed on the sample input channel 4 and the sample recovery channel 5, and be connected by electric wire. The voltage application means 33 is not particularly limited provided it is an item that can flow a DC current in the drive circuit 30 and move a sample, but it is preferably an item not susceptible to outputting noise, such as a battery box, etc.

With the embodiment shown in FIG. 15, the electrodes 31 and 32 are input in the sample input channel 4 and the sample recovery channel 5 of the device for electrical measurement 1 and the sample is moved, but as long as the sample can move, other embodiments are also possible. For example, by opening a hole in a portion of the sample recovery channel 5, connecting one end of a silicon tube to the sample recovery channel 5, and connecting the other end to the aspirator of a syringe pump, etc., in addition to the drive circuit 30, it is also possible to move the sample using suction force. This is also useful when using large samples such as cells, etc. It is also acceptable to not provide the sample input channel 4 and the sample recovery channel 5. In that case, a hole is formed in the sample separation channel 11 and the sample migration channel 3, the first electrode 31 of the drive circuit 30 is inserted in the sample separation channel 11, and the second electrode 32 is inserted in the sample migration circuit 3. Furthermore, as necessary, it is possible to provide the same kind of aspirator as noted above in the hole of one end of the sample migration channel 3, to connect one end of the silicon tube to the hole of the sample separation channel 11, and to connect the other end of that silicon tube to a sample liquid container, moving the sample using suction force in addition to the drive circuit 30.

When forming the first measuring unit 6 and the second measuring unit 7 with channels, the measuring circuit 40 includes at least a third electrode 41 inserted in the first measuring unit 6, a fourth electrode 42 inserted in the second measuring unit 7, and an ammeter 43, with the current from the third electrode 41 and the fourth electrode 42 measured using the ammeter 43.

Also, when performing high sensitivity detection by having the voltage of the drive circuit 30 and the measuring circuit 40 in a balanced state, and detecting the difference in current from the balanced state, by including in the measuring circuit 40 a voltage application means 44, a variable resistor 45, a resistance element 46 with a set resistance value, and also an amplification means as necessary, it is possible to measure only the current difference. More specifically, by operating the resistance value of the variable resistor 45 under a fixed voltage, it is possible to change each potential difference of the resistance element 46 and the variable resistor 45. By having the potential difference of the part sandwiched by the first measuring unit 6 and the second measuring unit 7 in the sample migration channel 3 and the potential difference of the resistance element 46 be balanced, based on Kirchhoff's law, a state is produced in which current does not flow to the part sandwiched between the first measuring unit 6 and the second measuring unit 7 in the sample migration channel 3, and the circuit including the resistance element 46, the first measuring unit 6, and the second measuring unit 7. When the sample flows in in this state, it is possible to measure the changes in current due to sample inflow as the difference from the state in which current does not flow.

The third electrode 41 and the fourth electrode 42 can be produced using the same material as the first electrode 31 and the second electrode 32, and they can be formed on the first measuring unit (channel) 6 and the second measuring unit (channel) 7 and connected with electric wire. The voltage application means 44, the same as with the voltage application means 33, is not particularly limited provided DC current flows to the measuring circuit 40, and a battery box, etc., can be used. For the ammeter 43 as well, a typically used ammeter can be used. For the amplification means as well, a typically used amp can be used. When forming the first measuring unit 6 and the second measuring unit 7 with electrodes, the third electrode 41 and the fourth electrode 42 are not required, and the electric wire connected to the ammeter 43 can be connected to the electrodes.

With the present embodiment, by using the variable resistor 45 and the resistance element 46, with the potential difference of the part sandwiched by the first measuring unit 6 and the second measuring unit 7 in the sample migration channel 3 and the potential different of the resistance element 46 in a balanced state, it is possible to measure the occurrence of transient current and changes in the steady-state current when the sample enters the sample migration channel 3 as displacement from the balanced state, so it is possible to increase the detection sensitivity. For the variable resistor 45 and the resistance element 46 used with the present embodiment, items available on the market can be used.

Figure 16:
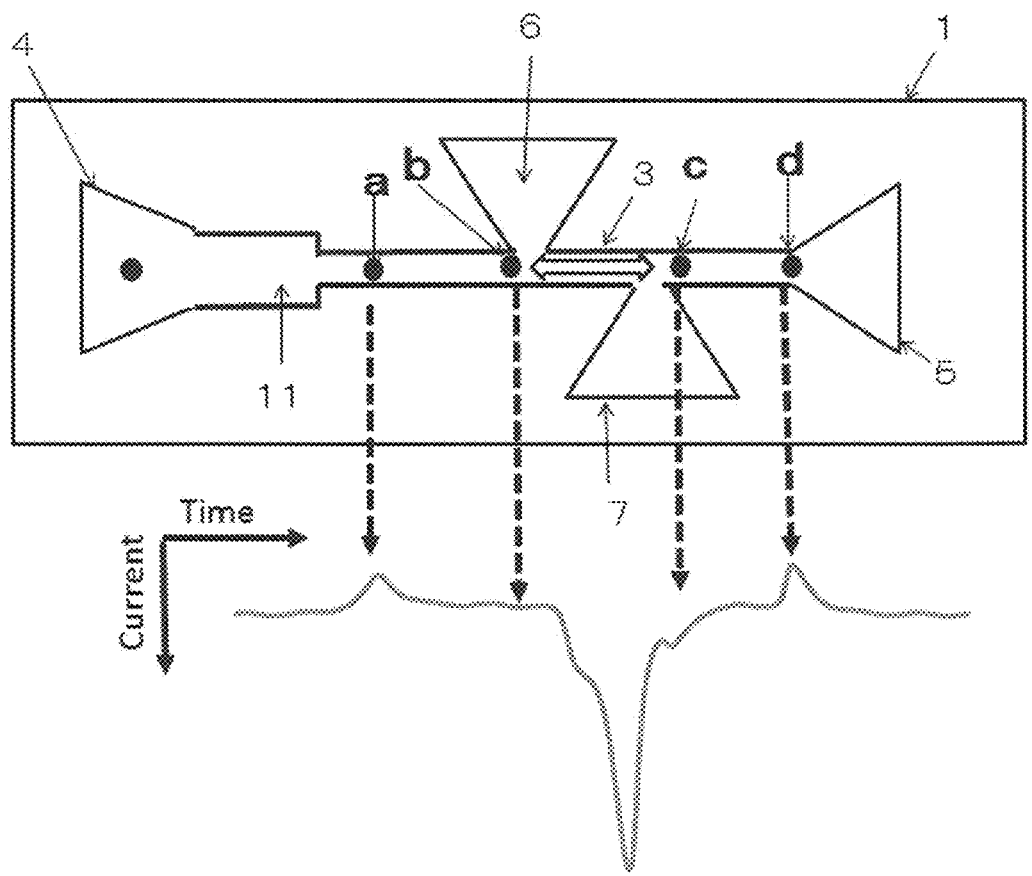
FIG. 16 is a diagram describing the relationship of the position of the sample on the device for electrical measurement 1 and the measurable current value when measuring the sample using the electrical measurement apparatus 10 of the present embodiment.

FIG. 16 is a diagram describing the relationship of the position of the sample on the device for electrical measurement 1 and the current value that can be measured when measuring samples using the electrical measurement apparatus 10 of the present embodiment. First, before measuring, a buffering solution such as PBS, phosphate buffer, TBE buffer, etc. is introduced into the channels using the capillary phenomenon, and next, the sample liquid is input into the sample input channel 4. Next, when voltage is applied to the drive circuit 30, the sample passes through the sample separation channel 11 and the sample migration channel 3, and moves toward the sample recovery channel 5. When the sample moves to near the boundary of the sample separation channel 11 and the sample migration channel 3 (position a in FIG. 16), the measuring circuit 40 first measures the transient current. Next, changes in the steady-state current are read until the sample moves from the position a to near the connecting part of the sample migration channel 3 and the first measuring unit 6 (position b in FIG. 16). Then, during the time from position b until the sample is output from the sample migration channel 3 and the second measuring unit 7 connecting part (position c in FIG. 16), larger changes in steady-state current are measured. Then, until the sample moves from position c to near the boundary of the sample migration channel 3 and the sample recovery channel 5 (position d in FIG. 16), changes in the steady-state current are read, and then, when the sample is output to the sample recovery circuit 5, the measuring circuit 40 measures the transient current.

As shown in FIG. 16, when the sample is measured using the device for electrical measurement 1 of the present embodiment, by measuring the transient current when the sample enters and when it exits the sample migration channel 3, it is possible to accurately measure the time for the sample to move through the sample migration channel 3 (a to d in FIG. 16). Therefore, it is possible to measure the surface charge and deformability, etc., of the sample.

Also, the particle diameter and shape of the sample can be measured by the size of changes in steady-state current during the time the sample goes from the connecting part of the first measuring unit 6 and the sample migration channel 3 to the connecting part of the second measuring unit 7 and the sample migration channel 3 (b to c in FIG. 16). Therefore, compared to the length of the sample migration channel 3, since the length for measuring the changes in the sample steady-state current is shorter, it is possible to maintain measurement sensitivity. Furthermore, since it is possible to use the sample migration channel 3 other than between the first measuring unit 6 and the second measuring unit 7 as a guide channel, it is possible to measure long molecules such as DNA, etc. in a stretched state with the measurement sensitivity maintained as is.

As noted above, the electrical measurement apparatus 10 of the present embodiment measures changes in steady-state current while the sample passes through the sample migration channel 3, and specifically, measures changes of larger steady-state current when the sample is moving between the first measuring unit 6 and the second measuring unit 7. Therefore, the first measuring unit 6 and the second measuring unit 7 can be formed at asymmetrical positions near both ends of the sample migration channel 3, but in that case, as shown by the embodiment described hereafter, since the waveform during the peak is linear, it is preferable to reduce the displacement of the positions at which the first measuring unit 6 and the second measuring unit 7 are formed. In the present specification, "displacement" of the position means the midpoint of the connecting part of the first measuring unit 6 and the sample migration channel 3 and the midpoint of the connecting part of the second measuring unit 7 and the sample migration channel 3 (white bidirectional arrow in FIG. 16). On the other hand, as shown in the embodiment described hereafter, even if the first measuring unit 6 and the second measuring unit 7 are formed at symmetrical positions flanking the sample migration channel 3, it is possible to measure the steady-state current, but since the waveform of the steady-state current is broken, as noted above, it is preferable to form them at asymmetrical positions, and it is more preferable to have the position displacement be the size of half the length of the connecting part of the first measuring unit 6 and the sample migration channel 3+half the length of the connecting part of the second measurement part 7 and the sample migration channel 3+the sample.

Figure 17:
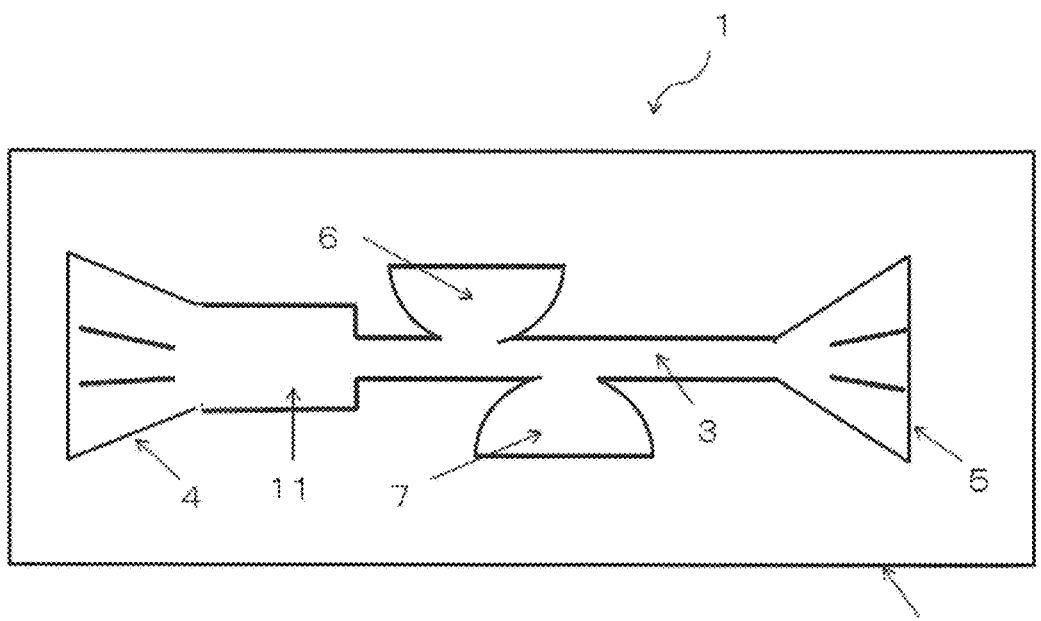
FIG. 17 shows another embodiment of the device for electrical measurement 1 of the present embodiment.

FIG. 17 is a diagram showing another embodiment of a device for electrical measurement 1. The sample input channel 4 and the sample recovery channel 5 of the device for electrical measurement 1 shown in FIGS. 3 to 5 are single channels, but as shown in FIG. 17, it is also possible to form the sample input channel 4 and the sample recovery channel 5 as a plurality of channels. By having the sample input channel 4 be a plurality of channels, for example, different samples can be input to individual channels, and by inputting the first electrode 31 and the second electrode 32 of the drive circuit to individual channels as well, and switching the electrode for applying voltage, it is possible to do continuous analysis of different samples, and recover to the sample recovery channel.

A plurality of channels can also be formed only for one of the sample input channel 4 or the sample recovery channel 5. When using a plurality of channels only for the sample input channel 4, it is possible to consecutively analyze different sample liquids.

Also, when samples with different surface charges are contained in the sample liquid, the movement speed of the sample flowing in the sample migration channel 3 is different. Therefore, by forming a plurality of channels for only the sample recovery channel 5, and switching the electrodes inserted in each channel, it is possible to do separation and recovery of different samples in the sample liquid, and possible to be used for yet another analysis.

Using the working examples below, specific examples of the present embodiment are explained, but these working examples are simply for describing the present embodiment, and are provided as reference for specific modes. These examples are for describing particular specific modes, but do not limit or express restriction of the scope of the invention disclosed in the application.

WORKING EXAMPLES

Production of Device for Electrical Measurement With Different Gaps for the First Measuring Unit 6 and the Second Measuring Unit 7

Working Example 1

First, to check the changes in measurement values of steady-state current and transient current due to differences in the gaps of the first measuring unit 6 and the second measuring unit 7, the device for electrical measurement was produced using the following procedure. In working examples 5 to 7 described hereafter, to study the changes in measurement values due to differences in gaps of the first measuring unit 6 and the second measuring unit 7, it is necessary to inflow samples into the sample migration channel 3 in the same state. Also, in working examples 9 and 10 described hereafter, to make it clear that it is possible to detect samples of different particle diameters using the device for electrical measurement of the present embodiment, it is necessary to inflow mixed samples of different particle diameters into the sample migration channel 3. Thus, since the sample separation channel is unnecessary, the sample separation channel was not formed on the device for electrical measurement of the working examples 1 to 3.

(1) A 600 μm thick silicon substrate 2 (made by Ferrotec Corp., 76 mm diameter) was prepared.

(2) Negative photoresist SU-8 3005 (made by Micro Chem Corp.) was coated using a spin coater.

(3) Using photolithography, to irradiate light on locations for forming channels, exposure was done using a photomask. After exposure, the resist was developed using SU-8 Developer (made by Micro Chem Corp.). After developing, rinsing was done using ultra pure water, moisture was sprayed off using a spin dryer to dry, and the casting mold was produced.

(4) Polydimethyl siloxane (PDMS: made by Toray Corp., SILPOT184) was flowed into the produced casting mold, and hardened.

(5) The hardened PDMS was removed from the casting mold, and next a cover glass available on the market (thickness: 0.17 mm) was adhered to the PDMS, to produce the device for electrical measurement 1.

Figure 18:
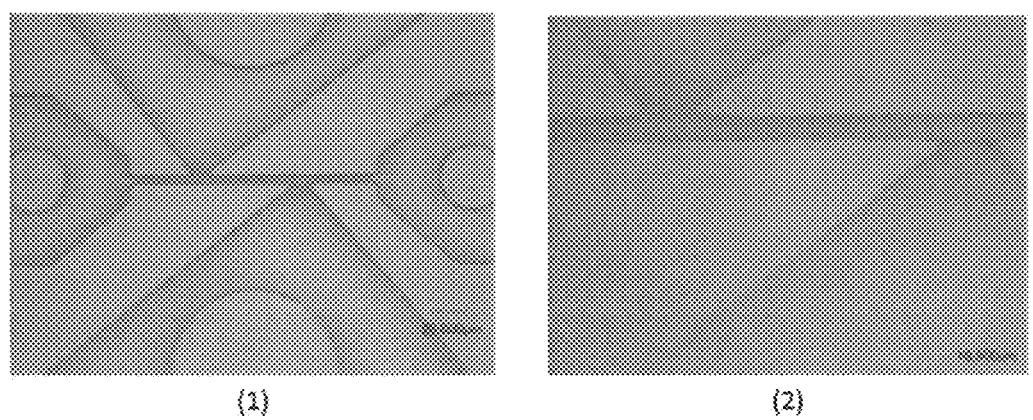
FIG. 18 shows drawing substitute photographs, with FIG. 18(1) being a photograph of the device for electrical measurement 1 produced with working example 1, and FIG. 18(2) being an enlarged photograph near the first measuring unit 6 and the second measuring unit 7.

FIG. 18(1) is a photograph of the device for electrical measurement 1 produced with working example 1, and FIG. 18(2) is an enlarged photograph near the first measuring unit 6 and the second measuring unit 7. The sample migration channel 3 length was 150 μm, the width 4 μm, and the depth 7.5 μm. With the first measuring unit 6 and the second measuring unit 7 depth at 7.5 μm, and the length of the connecting part with the sample migration channel 3 at 10.5 μm, the angle of the sample migration channel with the first measuring unit was approximately 45°. Also, the displacement of the first measuring unit 6 and the second measuring unit 7 flanking the sample migration channel 3 was 40 μm. The depth of the sample input channel 4 and the sample recovery channel 5 was 7.5 μm.

Working Example 2

Figure 19:
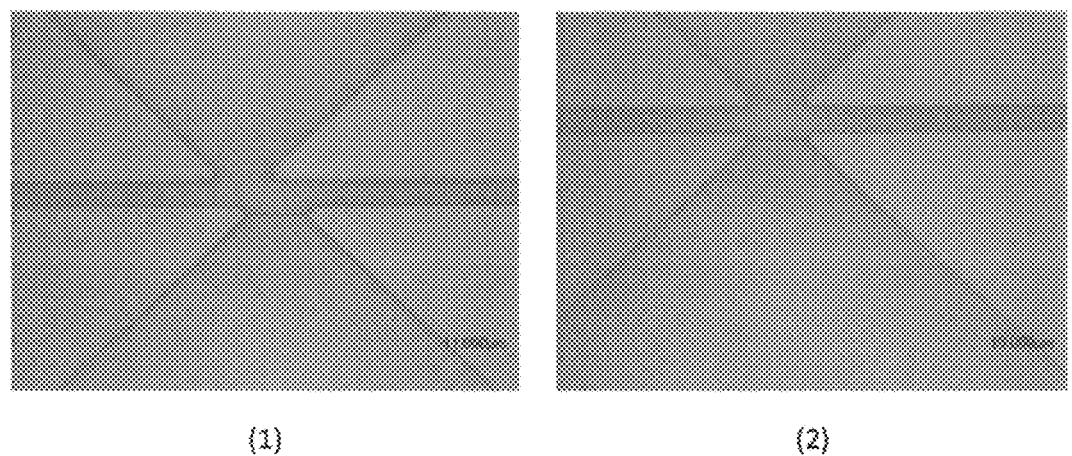
FIG. 19 shows drawing substitute photographs, with FIG. 19(1) being an enlarged photograph near the first measuring unit 6 and the second measuring unit 7 of the device for electrical measurement 1 produced with working example 2, and FIG. 19(2) being an enlarged photograph near the first measuring unit 6 and the second measuring unit 7 of the device for electrical measurement 1 produced with working example 3.

Other than changing the shape of the photomask of working example 1, and making the displacement of the first measuring unit 6 and the second measuring unit 7 be 5 µm, the device for electrical measurement 1 was produced using the same procedure as working example 1. FIG. 19(1) is an enlarged photograph near the first measuring unit 6 and the second measuring unit 7 of the device for electrical measurement 1 produced with working example 2.

Working Example 3

Other than changing the shape of the photomask of working example 1, and forming the first measuring unit 6 and the second measuring unit 7 at symmetrical positions flanking the sample migration channel 3, the device for electrical measurement 1 was produced using the same procedure as working example 1. FIG. 19(2) is an enlarged photograph near the first measuring unit 6 and the second measuring unit 7 of the device for electrical measurement 1 produced with working example 3.

Producing the Electrical Measurement Apparatus 10

Working Example 4

(1) Producing the Drive Circuit 30

The first electrode 31 and the second electrode 32 were produced by peeling the skin of an electric wire (FTVS-408, made by Oyaide Electric Co.) and exposing the metal part. A battery box (made by Seinan Industries Co.) was used for the voltage application means 33.

(2) Producing the Measuring Circuit 40

The third electrode 41 and the fourth electrode 42 were produced by peeling the skin of an electric wire (FTVS-408, made by Oyaide Electric Co.) and exposing the metal part. For the amplifying means, a variable gain low noise current amplifier made by FEMTO Co. was used. A battery box (made by Seinan Industries Co.) was used for the voltage application means 44. A precision potentiometer made by BI Technologies Co. was used for the variable resistor 45. For the ammeter 43, a signal amplified by the amplification means was converted to electrical signals for PC using a USB-DAQ (made by National Instruments Corp.), and this was read by software created using Lab View (made by National Instruments Corp.). For the resistance element 46, a metal film resistor (1 kΩ, made by Panasonic) was used.

(3) By inserting the first electrode 31 into the sample input channel 4, the second electrode 32 into the sample recovery channel 5, the third electrode 41 into the first measuring unit 6, and the fourth electrode 42 into the second measuring unit 7 of the device for electrical measurement 1 produced with working example 1, the electrical measurement apparatus 10 of the present embodiment was produced.

Measuring Using the Electrical Measurement Apparatus 10

Working Example 5

Figure 20:
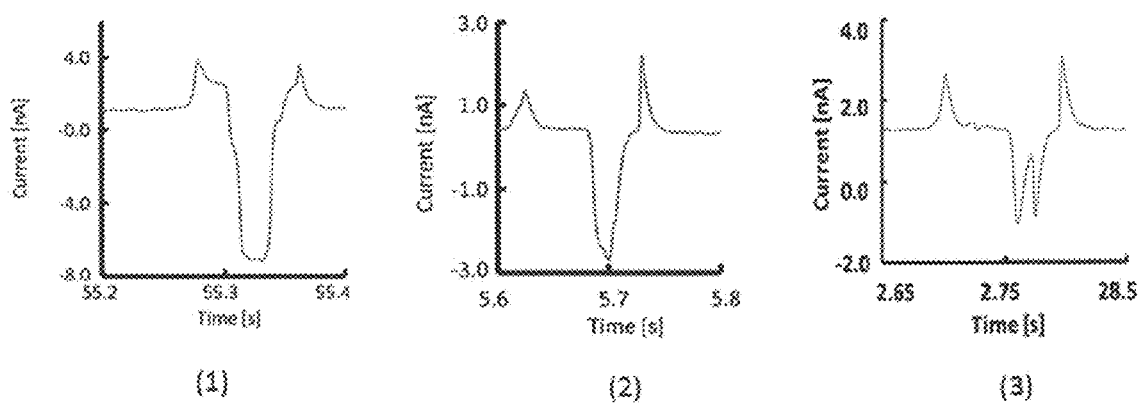
FIG. 20(1) is a graph showing the relationship between the measurement time and the measured steady-state current value in working example 5, FIG. 20(2) is a graph showing the relationship between the measurement time and the measured steady-state current value in working example 6, and FIG. 20(3) is a graph showing the relationship between the measurement time and the steady-state current value in working example 7.

The sample liquid was produced by dispersing fluorescent microbeads (Fluoresbrite made by Polyscience Co.) as the sample in ultra pure water. Next, a 5×TBE buffer was introduced in the channel by the capillary phenomenon, 30 µl of the produced sample liquid was input to the sample input channel 4, and a 53 V voltage was applied to the drive circuit 30. Also, an 18 V voltage was applied to the measuring circuit 40. The variable resistor 45 was operated, putting the apparent resistance of the drive circuit 30 and the measuring circuit 40 in a balanced state. The changes in steady-state current and occurrence of transient current when the sample flowed in the sample migration channel 3 was measured. FIG. 20(1) is a graph showing the relationship between the measurement time and the measured steady-state current value in working example 5.

Working Example 6

Other than using the device for electrical measurement 1 that was produced with working example 2, measurement was performed with the same procedure as working example 5. FIG. 20(2) is a graph showing the relationship between the measurement time and the measured steady-state current value in working example 6.

Working Example 7

Other than using the device for electrical measurement 1 produced with working example 3, measurement was performed using the same procedure as working example 5. FIG. 20(3) is a graph showing the relationship between the measurement time and the measured steady-state current value in working example 7.

As shown in FIGS. 20(1) to (3), even when using the device for electrical measurement 1 of any of working examples 1 to 3, two peaks of transient current are confirmed, and the gap between peaks was almost the same. Since the working examples 1 to 3 use the same samples, the surface charge is the same. Therefore, regardless of the positional relationship of the first measuring unit 6 and the second measuring unit 7, it is possible to accurately measure the time for the sample to move through the sample migration channel 3 according to the surface charge of the sample.

Also, when using the device for electrical measurement 1 of working example 1, as shown in FIG. 20(1), the change volume of the steady-state current value was greatest, but the waveform during the peak was linear. This is thought to be because since the displacement between the first measuring unit 6 and the second measuring unit 7 is large, even when the sample moved between the first measuring unit 6 and the second measuring unit 7, volume change did not occur, and a steady-state continued.

On the other hand, as shown in FIG. 20(2), when using the device for electrical measurement 1 of working example 2, compared to the device for electrical measurement 1 of working example 1, though there is less change in the steady-state current value, a clear peak was shown in the waveform of the steady-state current value.

Figure 21:
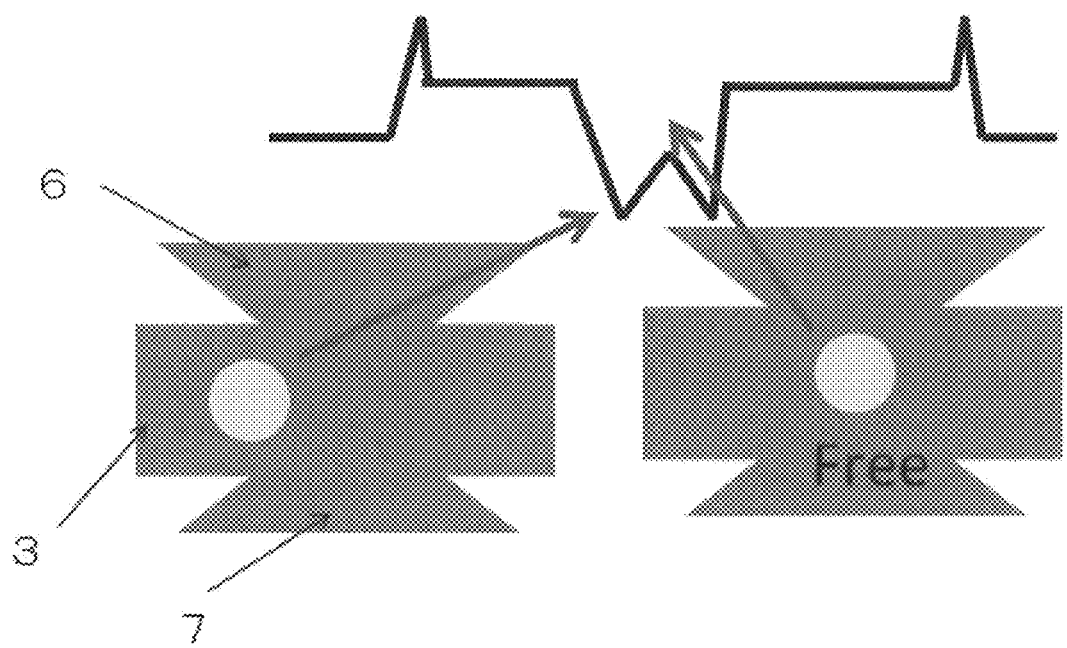
FIG. 21 is a diagram describing the reason two peaks are measured when using the device for electrical measurement 1 of working example 3.

Furthermore, when using the device for electrical measurement 1 of working example 3, two peaks were measured as shown in FIG. 20(3). This is believed to be because, as shown in FIG. 21:

(1) The first measuring unit 6 and the second measuring unit 7 are arranged in a symmetrical positional relationship, so it is easy for current of the measuring circuit 40 to flow compared with the arrangements of working example 1 and working example 2, (2) the change in the steady-state current was measured when the sample flowed out to the end of the first measuring unit 6 and the second measuring unit 7, but as noted above, since it is easy for electricity to flow with the device for electrical measurement 1 of the working example 3, the steady-state current value when the sample comes to the middle of the connecting part with the sample migration channel 3 returns to a value close to the base value, (3) and when the sample flows out from the connecting part, changes in the steady-state current value was measured.

From the results above, the first measuring unit 6 and the second measuring unit 7 are preferably formed at asymmetrical positions flanking the sample migration channel 3, and are preferably arranged with a displacement to the degree that the peak value will not be a linear value according to the sample size (the end parts of the first measuring unit 6 and the second measuring unit 7 are at positions where they do not overlap flanking the sample migration channel 3, and are not too far apart).

Measurement Using the Electrical Measurement Apparatus 10 and a Fluorescence Microscope Working Example 8

Figure 22:
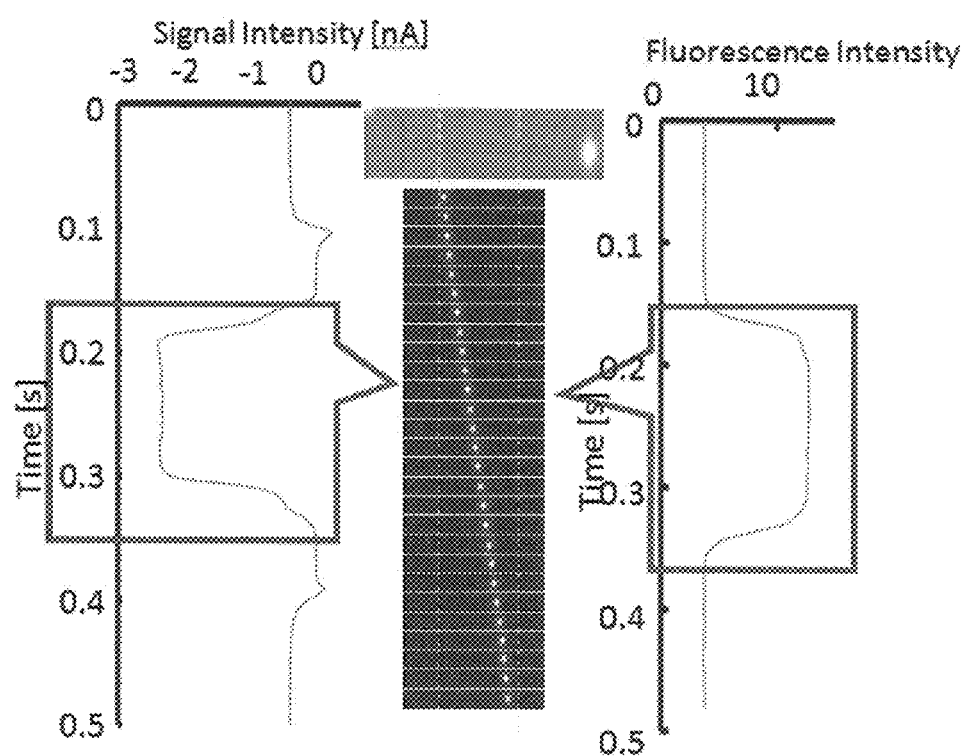
FIG. 22 shows a sequence photo of the position of the sample flowing in the sample migration channel 3, and a photograph and a graph showing changes in the steady-state current value (signal intensity) and changes in the fluorescence intensity when the sample flows.

Other than using fluorescent microbeads (Fluoresbrite made by Polyscience Co.) as the sample, and measuring fluorescence intensity with a fluorescence microscope (TE300 made by Nikon Corp.) arranged to be able to observe between the first measuring unit 6 and the second measuring unit 7 of the device for electrical measurement 1, measurement was performed with the same procedure as working example 5. FIG. 22 includes a photograph of the device for electrical measurement 1, a photograph of fluorescent microbeads flowing between the first measuring unit 6 and the second measuring unit 7, and a graph showing changes in the steady-state current value (signal intensity) and changes in fluorescence intensity when the fluorescent microbeads flow (the parts enclosed by a line in the graph are the measurement results when the fluorescent microbeads flowed between the first measuring unit 6 and the second measuring unit 7). As shown in FIG. 22, by using the electrical measurement apparatus 10 of the present embodiment, it is possible to observe the sample flowing in the sample migration channel 3 of the device for electrical measurement 1 with the fluorescence microscope while measuring transient current and steady-state current value changes, so it is possible to accurately observe the phenomena occurring at the measurement site of the device for electrical measurement 1.

Working Example 9

Figure 23:
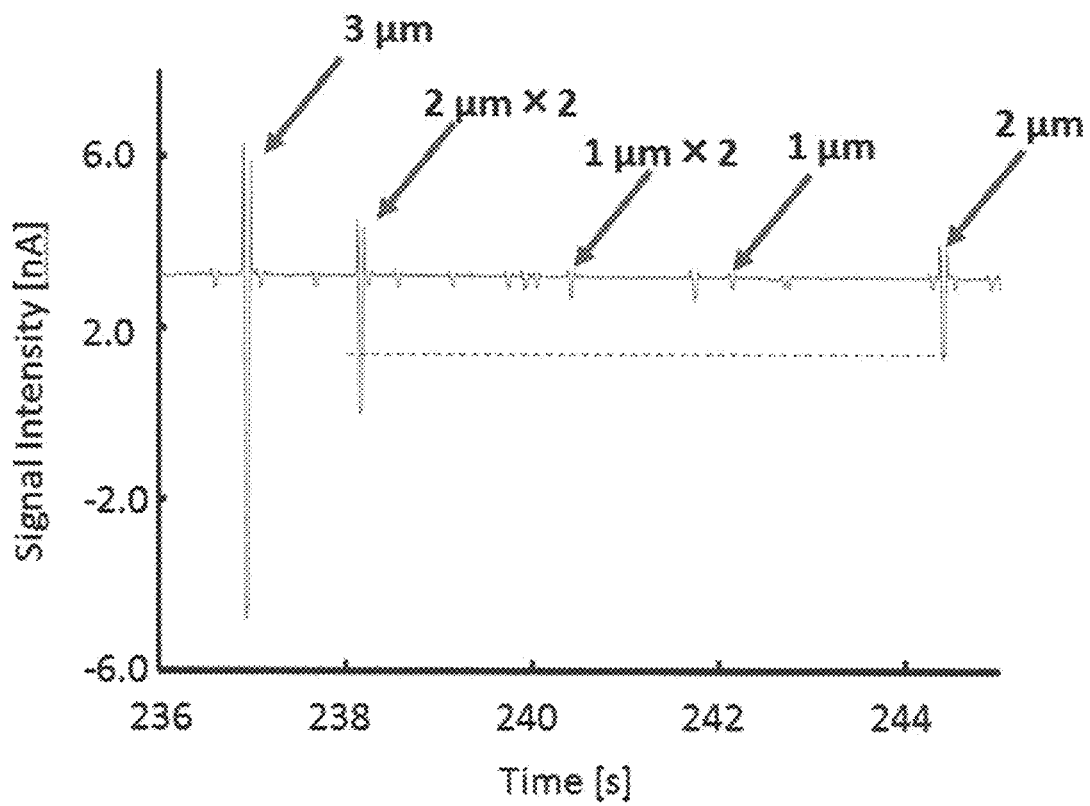
FIG. 23 is a graph showing changes in the steady-state current value (signal intensity) measured with working example 9.

Other than using fluorescent microbeads (Fluoresbrite made by Polyscience Co.) of particle diameters of approximately 3.1 μm, 2.08 μm, and 1 μm as the sample, measurement was performed using the same procedure as working example 8. FIG. 23 is a graph showing changes in the steady-state current value (signal intensity) measured with working example 9. With only measurement of changes of the steady-state current value as in the past, it was difficult to differentiate whether substances of the same sizes are overlapped or whether they are substances of different sizes, but by observing with the fluorescence microscope together, it became possible to accurately differentiate samples. Since the fluorescence microscope is able to differentiate different colors, for example, while observing dyed Gram-negative bacteria and Gram-positive bacteria using the fluorescence microscope, it is possible to differentiate general types by measuring transient current and steady-state current changes.

Relationship Between the Particle Diameter and Steady-State Current Value

Working Example 10

Figure 24:
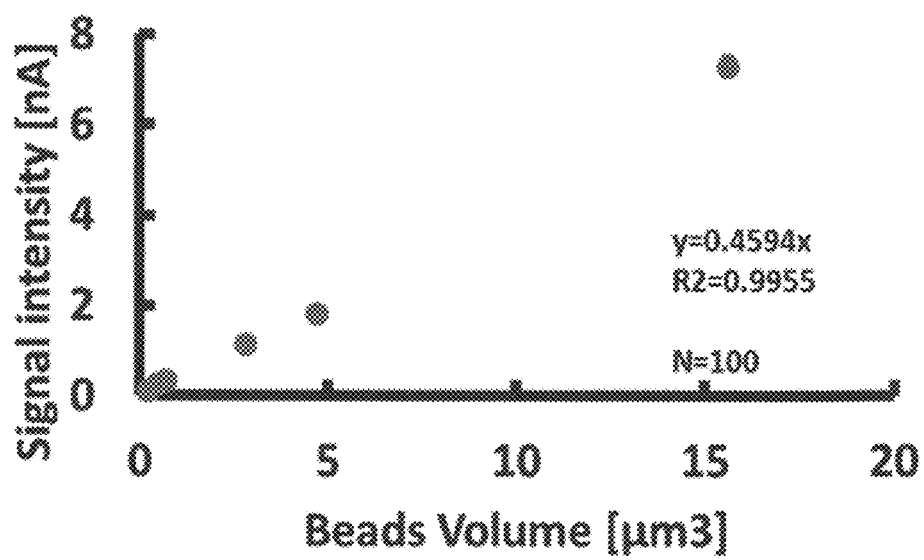
FIG. 24 is a graph showing the volume of the sample produced based on results measured with working example 9 and steady-state current value (signal intensity) changes.

Using fluorescent microbeads (Fluoresbrite made by Polyscience Co.) of particle diameters of approximately 3.1 μm, 2.08 μm, 1.75 μm, 1.1 μm, 1 μm, and 0.75 μm as the samples, measurement was performed using the same procedure as working example 9. FIG. 24 is a graph showing the sample volume and steady-state current value changes (signal intensity). As shown in FIG. 24, it was confirmed that there is a correlation between signal intensity and the sample volume.

Relationship Between Applied Voltage, Signal Intensity, and Passage Time

Working Example 11

Figure 25:
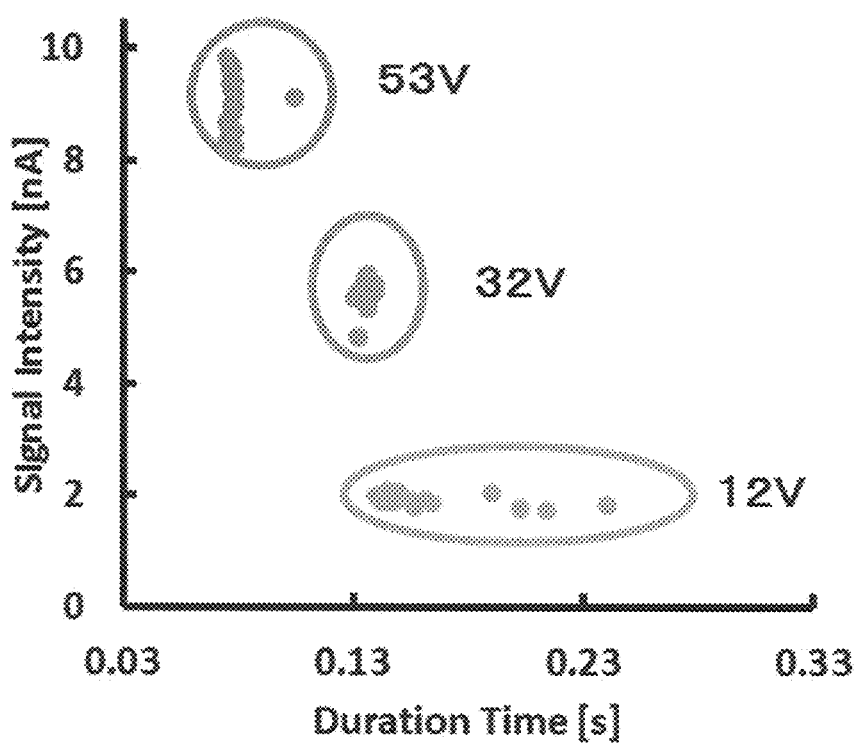
FIG. 25 is a diagram showing the relationship between the drive circuit voltage and the time for the sample to pass through the sample migration channel.

Other than measuring the three voltages of 53 V, 32 V, and 12 V for the voltage of the drive circuit 30 in working example 5, measurement was performed with the same procedure as with working example 5. FIG. 25 is a diagram showing the relationship between the drive circuit voltage and the time for the sample to pass through the sample migration channel. As shown in FIG. 25, while it is possible to increase measurement sensitivity by making the voltage of the drive circuit 30 bigger, it became clear that the passage time became shorter according to the surface charge of the sample. Also, in the case of 12 V, though there was little variation in signal intensity, the variation in passage time was great. On the other hand, when the drive voltage was 32 V or greater, there was almost no variation in passage time, but variation was seen in signal intensity. This is thought to be because under low voltage, the drive force to the sample having charge becomes lower, and there is an effect on the sample movement speed by frictional force received from the wall surface.

In the present embodiment, the length of the sample migration channel 3, and the gap of the first measuring unit 6 and the second measuring unit 7 can be set freely. Therefore, even if the voltage of the drive circuit 30 is made high, it is possible to set the length of the sample migration channel 3 as well as the first measuring unit 6 and the second measuring unit 7 so that the shortest time required to read the steady-state current changes is set, and possible to perform high sensitivity detection in a short time.

Producing the Device for Electrical Measurement Including the Sample Separation Channel Working Example 12

(1) A 380 μm thick silicon substrate (76 mm diameter, made by Ferrotec Corp.) was prepared.

(2) A mask was produced using OFPR8600 to make a shape that can be etched for the various channels including the sample separation channel, as well as the parts other than the pillars inside the sample separation channel.

(3) Next, by dry etching using an ICP etching device (made by Samco Inc.), the device for electrical measurement 1 was produced.

Figure 26:
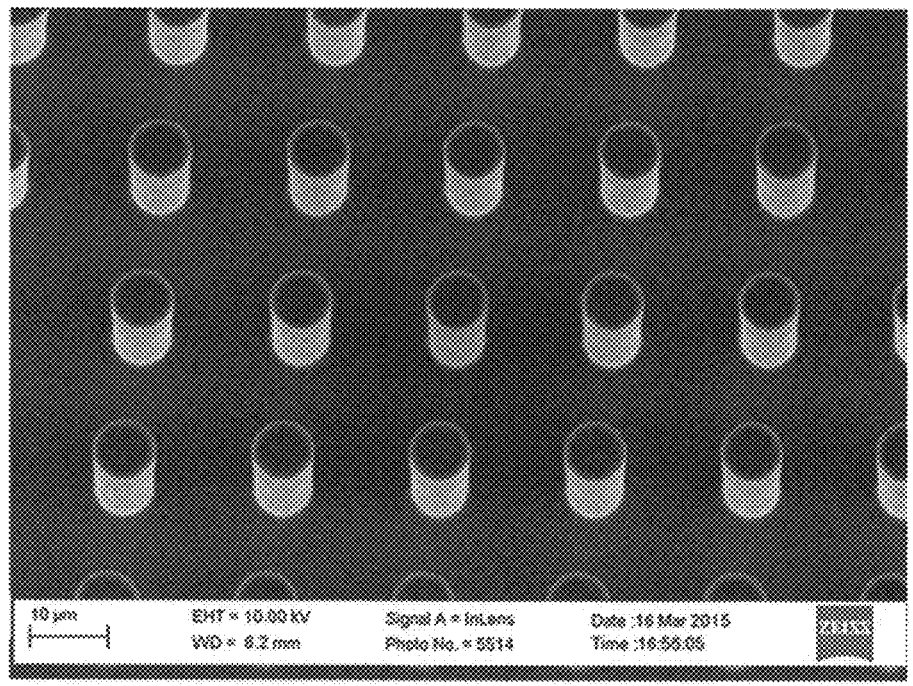
FIG. 26 shows drawing substitute photographs, with FIG. 26(1) being a photograph of the sample separation channel 11 part of the device for electrical measurement 1 produced with working example 12, and FIG. 26(2) being a photograph with a portion of the pillars enlarged.
Figure 26:
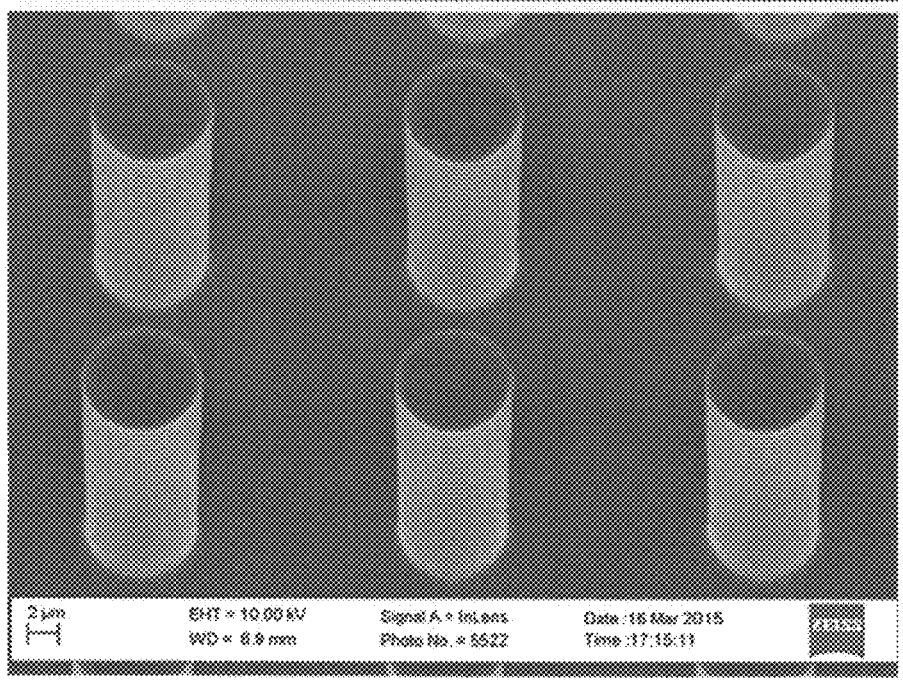

FIG. 26(1) is a photograph of the sample separation channel 11 part of the device for electrical measurement 1 produced with working example 12, and FIG. 26(2) is a photograph with a portion of the pillars enlarged. The pillar diameter is approximately 10 μm, the height (depth of the sample separation channel) is approximately 20 μm, and the gap between adjacent pillars (gap between the pillar outer circumferences) is approximately 10 μm. Also, the angle of the wall surface of the sample separation channel 11 and the pillar row was approximately 1.6°.

Producing the Device for Electrical Measurement With Electrodes Formed to Cut Across the Sample Migration Channel 3

Working Example 13

First, the seal member 22 on which electrodes are formed (the first measuring unit 6 and the second measuring unit 7) was produced using the following procedure.

(1) OAP which becomes an adhesive layer (made by Tokyo Ohka Kogyo Co.) was coated on silica glass (made by Crystal Base Co.), and positive photoresist OFPR8600 (Tokyo Ohka Kogyo Co.) was coated using a spin coater.

(2) Using photolithography, a photomask was used and exposure was done so that light would irradiate on locations for forming the first measuring unit 6 and the second measuring unit 7. After exposure, the resist was developed using NMD-3. After developing, rinsing was done using ultra pure water.

(3) The seal material 22 was produced by depositing Ti at 10 nm and Pt at 120 nm on the part at which the positive photoresist 9 was removed using a sputtering device (made by Sanyu Electron).

Figure 27:
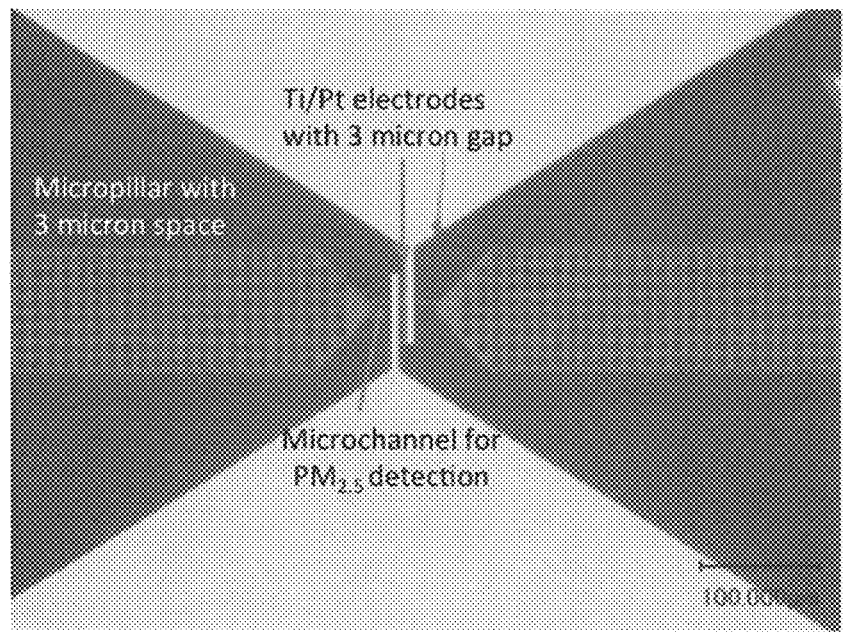
FIG. 27 is a diagram substitute photograph, and is a photograph of the device for electrical measurement 1 produced with working example 13 taken with an inverted microscope from the seal material 22 side.

Next, using the same procedure as working example 12, the substrate 2 on which pillars are formed in the sample separation channel 11 was produced, and the substrate 2 and the seal material 22 were adhered together so that the electrodes formed on the seal material 22 (the first measuring unit 6 and the second measuring unit 7) cut across the sample migration channel 3. FIG. 27 is a photograph taken from the seal material 22 side using an inverted microscope of the device for electrical measurement 1 produced with working example 13. The gap between the first measuring unit 6 and the second measuring unit 7 was approximately 3 μm. Also, the width of the sample migration channel 3 was set to 3 μm for measuring PM2.5.

Electrical Measurement Apparatus 10 Production and Measurement

Working Example 14

Figure 28:
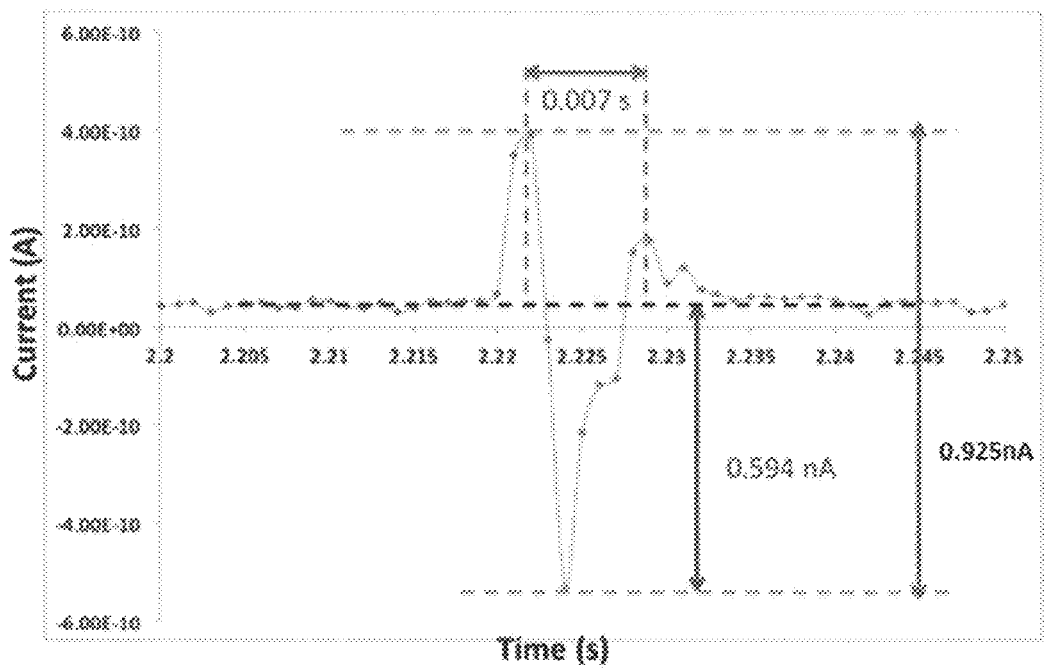
FIG. 28 is a graph showing the relationship between the measuring time and the measured steady-state current value in working example 14.

Next, other than using the device for electrical measurement 1 produced with working example 13, the electrical measurement apparatus 10 was produced using the same procedure as working example 4. Other than using for the sample an item for which a standard substance of PM2.5 (National Institute for Environmental Studies CRM No. 28, urban particulate matter) was dispersed in 0.1 M KCl, and using 6 V as the voltage applied to the drive circuit 30 and 1.5 V as the voltage applied to the measuring circuit 40, measurement was performed using the same procedure as working example 5. FIG. 28 is a graph showing the relationship between the measurement time and the measured steady-state current value in working example 14. As shown in FIG. 28, it was possible to measure two transient current peaks (time between peaks: 0.007 s) and changes in the steady-state current value.

From the above results, it became clear that the electrodes configuring the measuring circuit can be formed flanking the sample migration channel 3 as shown in FIG. 5, and can also be formed cutting across the sample migration channel 3 as shown in FIG. 6 and FIG. 7.

INDUSTRIAL APPLICABILITY

By using the device for electrical measurement 1 of the present embodiment, it is possible to design the drive circuit and the measuring circuit as separate circuits, so it is possible to set the voltage of the drive circuit high, and to increase the detection sensitivity. Furthermore, since it is possible to accurately read the transient current, it is possible to read the surface charge of the sample, and it is also possible to create a stretched state of the sample inside the sample migration channel, and to measure biomolecules such as of nucleic acid, protein, etc. Furthermore, it is possible to separate samples before measuring.

Therefore, this is useful in developing measurement equipment for doing accurate analysis of samples in companies and research institutions, etc.

What is claimed is:

1. An electrical measurement apparatus, comprising:
a device for electrical measurement;
a drive circuit; and
a measuring circuit, wherein:
the device for electrical measurement comprises a substrate including:
a sample migration channel thorough which a sample moves and a sample measuring unit formed on the substrate,
a sample input channel disposed on an upstream side of the sample migration channel, and
a sample recovery channel disposed on a downstream side of the sample migration channel,
a width of the sample migration channel is constant,
the sample measuring unit comprises a first measuring unit connected to the sample migration channel at a first point of the sample migration channel, and a second measuring unit connected to the sample migration channel at a second point of the sample migration channel downstream of the first point,
the drive circuit comprises a first electrode placed in the sample input channel and a second electrode placed in the sample recovery channel, and is configured to apply a potential difference between the first electrode and the second electrode such that an ionic current flows through the sample migration channel,
the measuring circuit is configured to measure a change in the ionic current when the sample moves in the sample migration channel sandwiched between the first electrode and the second electrode,
the first measuring unit and the second measuring unit are connected to the sample migration channel between the first electrode and the second electrode,
the first measuring unit includes a third electrode and the second measuring unit includes a fourth electrode,
the measuring circuit is coupled to the third electrode and the fourth electrode,
the measuring circuit further comprises:
a variable resistor; and
a resistance element sandwiched between the first measuring unit and the second measuring unit, and
a potential difference between both ends of the resistance element is adjusted by operating the variable resistor.

2. The electrical measurement apparatus of claim 1, wherein the first point is located on a first side of the sample migration channel and the second point is located on a second side of the sample migration channel opposite to the first side.

3. The electrical measurement apparatus of claim 1, wherein:
the device for electrical measurement further comprises a sample separation channel disposed between the sample input channel and the sample migration channel.

4. The electrical measurement apparatus of claim 3, wherein pillars are formed in the sample separation channel.

5. The electrical measurement apparatus of claim 3, wherein:
the device for electrical measurement further comprises a separated sample discharge channel for discharging separated and removed elements in the sample, and
the separated sample discharge channel is connected to the sample separation channel.

6. The electrical measurement apparatus of claim 1, wherein the device for electrical measurement further comprises a sample collecting apparatus for collecting samples.

7. The electrical measurement apparatus of claim 6, wherein the sample collecting apparatus includes an inclined sample collecting unit, and a sample input hole formed on the top part of the inclined sample collecting unit, for inputting collected samples into the sample input channel.

8. The electrical measurement apparatus of claim 7, wherein cones are formed on the inclined sample collecting unit.

9. The electrical measurement apparatus of claim 7, wherein nanowires are formed on the inclined sample collecting unit.

10. The electrical measurement apparatus of claim 1, wherein the measuring circuit measures a transient current and steady-state current changes.

11. The electrical measurement apparatus of claim 1, further comprising a fluorescence microscope.

* * * * *